US010781446B2

(12) United States Patent
Guo et al.

(10) Patent No.: US 10,781,446 B2
(45) Date of Patent: Sep. 22, 2020

(54) RNA NANOPARTICLE FOR TREATMENT OF GASTRIC CANCER

(71) Applicants: UNIVERSITY OF KENTUCKY RESEARCH FOUNDATION, Lexington, KY (US); Daxiang Cui, Shanghai (CN); Chunlei Zhang, Shanghai (CN)

(72) Inventors: Peixuan Guo, Columbus, OH (US); Daxiang Cui, Shanghai (CN); Dan Shu, Columbus, OH (US); Yi Shu, Lexington, KY (US); Chunlei Zhang, Shanghai (CN)

(73) Assignee: University of Kentucky Research Foundation, Lexington, KY (US)

( * ) Notice: Subject to any disclaimer, the term of this patent is extended or adjusted under 35 U.S.C. 154(b) by 68 days.

(21) Appl. No.: 15/556,946

(22) PCT Filed: Mar. 9, 2016

(86) PCT No.: PCT/US2016/021444
§ 371 (c)(1),
(2) Date: Sep. 8, 2017

(87) PCT Pub. No.: WO2016/145003
PCT Pub. Date: Sep. 15, 2016

(65) Prior Publication Data
US 2019/0032050 A1    Jan. 31, 2019

Related U.S. Application Data

(60) Provisional application No. 62/130,527, filed on Mar. 9, 2015.

(51) Int. Cl.
*C12N 15/113* (2010.01)
*C07H 21/04* (2006.01)
*C12N 15/11* (2006.01)
*C12N 15/115* (2010.01)
*A61P 35/00* (2006.01)

(52) U.S. Cl.
CPC ............ *C12N 15/113* (2013.01); *A61P 35/00* (2018.01); *C07H 21/04* (2013.01); *C12N 15/111* (2013.01); *C12N 15/115* (2013.01); *C12N 2310/14* (2013.01); *C12N 2310/16* (2013.01); *C12N 2310/3519* (2013.01); *C12N 2310/52* (2013.01); *C12N 2320/32* (2013.01)

(58) Field of Classification Search
CPC ... C12N 15/111; C12N 15/113; C12N 15/115; C12N 2310/14; C12N 2310/16
See application file for complete search history.

(56) References Cited

U.S. PATENT DOCUMENTS

| 6,180,082 B1 | 1/2001 | Woltering et al. |
| 6,506,559 B1 | 1/2003 | Driver et al. |
| 9,297,013 B2 * | 3/2016 | Guo ............... C12N 15/111 |
| 2005/0221371 A1 | 10/2005 | Bougueleret |
| 2010/0323018 A1 | 12/2010 | Irvine et al. |
| 2011/0053862 A1 | 3/2011 | Xie et al. |
| 2011/0275785 A1 | 11/2011 | Mixson |
| 2012/0277163 A1 | 11/2012 | Gaur et al. |
| 2013/0177556 A1 | 7/2013 | De Franciscis et al. |
| 2014/0045709 A1 | 2/2014 | Croce et al. |
| 2014/0179758 A1 | 6/2014 | Guo |
| 2014/0186430 A1 | 7/2014 | Gould-Fogerite |

FOREIGN PATENT DOCUMENTS

| CN | 104327141 | 2/2015 | |
| WO | 07409 | 2/1999 | |
| WO | 32619 | 7/1999 | |
| WO | 01846 | 1/2000 | |
| WO | 44895 | 8/2000 | |
| WO | 44914 | 8/2000 | |
| WO | 29058 | 4/2001 | |
| WO | 36646 | 5/2001 | |
| WO | WO-2012170372 A2 * | 12/2012 | ........... C12N 15/111 |
| WO | 167112 | 3/2013 | |

OTHER PUBLICATIONS

Leng et al. The Journal of Gene Medicine 7: 977-986 (Year: 2005).*
Stedman, Thomas Lathrop, "Stedman's Medical Dictionary" (27th edition, 2000).
Cui et al. "Characterization of BRCAA 1 and its Novel Antigen Epitope Identification," Cancer Epidemiology Biomarkers & Prevention, Jul. 1, 2004 (Jul. 1, 2004), vol. 13, No. 7, pp. 1136-1145. entire document.
Cui et al. "Regression of Gastric Cancer by Systemic Injection of RNA Nanoparticles Carrying Both Ligand and siRNA," Scientific Reports, Jul. 3, 2015 (Jul. 3, 2015), vol. 5, pp. 1-14. entire document.
International Search Report dated Jul. 12, 2016.
Written Opinion of the ISA dated Jul. 12, 2016.
Abdelmawla, S. et al. Pharmacological characterization of chemically synthesized monomeric phi29 pRNA nanoparticles for systemic delivery. Molecular therapy : the journal of the American Society of Gene Therapy. 19, 1312-1322 (2011).

(Continued)

*Primary Examiner* — Brian Whiteman
(74) *Attorney, Agent, or Firm* — Baker Donelson

(57) ABSTRACT

The presently-disclosed subject matter relates to RNA-based composition and method to treat gastric cancer in a subject. More particularly, the presently disclosed subject matter relates to a RNA nanostructure and composition containing a multiple branched RNA nanoparticle, a gastric cancer targeting module, and an effective amount of a therapeutic agent. Further, the presently disclosed subject matter relates to a method of using the RNA nanoparticle composition to treat gastric cancer in a subject having or at risk of having gastric cancer.

26 Claims, 9 Drawing Sheets

Specification includes a Sequence Listing.

(56) References Cited

OTHER PUBLICATIONS

Bass, Brenda L. "RNA interference: The short answer." Nature411. 6836 (2001): 428-429.
Chen, F. et al. The photoluminescence, drug delivery and imaging properties of multifunctional Eu3t/Gd3t dual-doped hydroxyapatite nanorods. Biomaterials. 32, 9031-9039 (2011).
Chen, J. et al. Differential Expression of Phospholipase C Epsilon 1 Is Associated with Chronic Atrophic Gastritis and Gastric Cancer PLoS One. 7, 10 (2012).
Chen, L. et al. Tumor-specific Expression of MicroRNA-26a Suppresses Human Hepatocellular Carcinoma Growth via Cyclin-dependent and -independent Pathways. Molecular Therapy. 19, 1521-1528 (2011).
Comis, R. L. & Carter, S.K. A review of chemotherapy in gastric cancer. Cancer. 34, 1576-1586 (1974).
Cui, D. X. et al. A microarray-based gastric carcinoma prewarning system. World J Gastroenterol. 11, 1273-82 (2005).
Dicken, B. J. et al. Gastric adenocarcinoma: review and considerations for future directions. Annals of surgery. 241, 27-39 (2005).
Elbashir, Sayda M., et al. "Duplexes of 21-nucleotide RNAs mediate RNA interference in cultured mammalian cells." nature 411. 6836 (2001): 494-498.
Ferlay, J. et al. Estimates of worldwide burden of cancer in 2008: GLOBOCAN 2008. Int. J. Cancer 127, 2893-2917 (2010).
Fire, Andrew, et al. "Potent and specific genetic interference by double-stranded RNA in Caenorhabditis elegans." nature 391.6669 (1998): 806-811.
Fu, H. L. et al. TET1 Exerts Its Tumor Suppressor Function by Interacting with p53-EZH2 Pathway in Gastric Cancer. J. Biomed. Nanotechnol. 10, 1217-1230 (2014).
Griffiths-Jones, Sam, et al. "miRBase: microRNA sequences, targets and gene nomenclature." Nucleic acids research34.suppl_1 (2006): D140-D144.
Guo, P. The emerging field of RNA nanotechnology. Nature nanotechnology. 5, 833-842 (2010).
Guo, P., Hague, F., Hallahan, B., Reif, R. & Li, H. Uniqueness, advantages, challenges, solutions, and perspectives in therapeutics applying RNA nanotechnology. Nucleic acid therapeutics. 22, 226-245 (2012).
Guo, P., Zhang, C., Chen, C., Garver, K. & Trottier, M. Inter-RNA interaction of phage phi29 pRNA to form a hexameric complex for viral DNA transportation. Molecular cell. 2, 149-155 (1998).
Haque, F. et al. Ultrastable synergistic tetravalent RNA nanoparticles for targeting to cancers. Nano today. 7, 245-257 (2012).
Huang, P. et al. Folic Acid-conjugated Graphene Oxide loaded with Photosensitizers for Targeting Photodynamic Therapy. Theranostics. 1, 240-250 (2011).
Huang, P. et al. Folic acid-conjugated Silica-modified gold nanorods for X-ray/CT imaging-guided dual-mode radiation and photothermal therapy. Biomaterials. 32, 9796-9809 (2011).
Huang, P. et al. Light-triggered theranostics based on photosensitizer-conjugated carbon dots for simultaneous enhanced-fluorescence imaging and photodynamic therapy. Adv. Mater 24, 5104-5110 (2012).
Jasinski, D.L., Khisamutdinov, E. F., Lyubchenko, Y.L., Guo, P. Physicochemically Tunable Polyfunctionalized RNA Square Architecture with Fluorogenic and Ribozymatic Properties. ACS Nano. 26, 7620-7629 (2014).
Jemal, A. et al. Global cancer statistics. CA Cancer J. Clin. 61, 69-90 (2011).
Kalli, K. R. et al. Folate receptor alpha as a tumor target in epithelial ovarian cancer. Gynecologic oncology. 108, 619-626 (2008).
Kappler, Matthias, et al. "Knockdown of survivin expression by small interfering RNA reduces the clonogenic survival of human sarcoma cell lines independently of p53." Cancer gene therapy 11.3 (2004): 186-193.
Khisamutdinov, E. F., et al. Enhancing immunomodulation on innate immunity by shape transition among RNA triangle, square and pentagon nanovehicles. Nucleic Acids Res. 42, 9996-10004 (2014).
Khisamutdinov, E. F., Jasinski, D. L. & Guo, P. RNA as a boiling-resistant anionic polymer material to build robust structures with defined shape and stoichiometry. ACS nano.8, 4771-4781 (2014).
Kuo, C. Y., Chao, Y. & Li, C. P. Update on treatment of gastric cancer. Journal of the Chinese Medical Association : JCMA. (2014).
Lei, Xiao-Yong, et al. "Silencing of Bcl-XL expression in human MGC-803 gastric cancer cells by siRNA." Acta biochimica et biophysica Sinica 37.8 (2005): 555-560.
Li, C. et al. BRCAA1 antibody- and Her2 antibody-conjugated amphiphilic polymerengineered CdSe/ZnS quantum dots for targeted imaging of gastric cancer Nanoscale Res. Lett. 9, 244 (2014).
Li, Z. M. et al. Aptamer-conjugated dendrimer-modified quantum dots for cancer cell targeting and imaging. Materials Letter. 64, 375-378 (2010).
Ly, A., Hoyt, L., Crowell, J. & Kim, Y. I. Folate and DNA methylation. Antioxidants & redox signaling. 17, 302-326 (2012).
Murphy, E. A. et al. Targeted nanogels: a versatile platform for drug delivery to tumors. Molecular cancer therapeutics. 10, 972-982 (2011).
Pan, B. F. et al. Synthesis and characterization of polyamidoamine dendrimer-coated multi-walled carbon nanotubes and their application in gene delivery systems. Nanotechnology. 20, 125101 (2009).
Proserpio, I. et al. Multimodal treatment of gastric cancer. World journal of gastrointestinal surgery. 6, 55-58 (2014).
Ruan J, Wang K, Song H, Xu X, Ji JJ, Cui D. Biocompatibility of hydrophilic silica-coated CdTe quantum dots and magnetic nanoparticles. Nanoscale Research Letters 2011;6:299.
Shu, D., Moll, W. D., Deng, Z., Mao, C. & Guo, P. Bottom-up Assembly of RNA Arrays and Superstructures as Potential Parts in Nanotechnology. Nano Letters. 4, 1717-1723 (2004).
Shu, D., Shu, Y., Haque, F., Abdelmawla, S. & Guo, P. Thermodynamically stable RNA three-way junction for constructing multifunctional nanoparticles for delivery of therapeutics. Nature nanotechnology. 6, 658-667 (2011).
Shu, Y. et al. Fabrication of 14 different RNA nanoparticles for specific tumor targeting without accumulation in normal organs. RNA (New York, N. Y.). 19, 767-777 (2013).
Shu, Y., Shu, D., Haque, F. & Guo, P. Fabrication of pRNA nanoparticles to deliver therapeutic RNAs and bioactive compounds into tumor cells. Nature protocols. 8, 1635-1659 (2013).
Spee, Bart, et al. "Specific down-regulation of XIAP with RNA interference enhances the sensitivity of canine tumor cell-lines to TRAIL and doxorubicin." Molecular Cancer 5.1 (2006): 34.
Takahashi, T., Saikawa, Y. & Kitagawa, Y. Gastric cancer: current status of diagnosis and treatment. Cancers (Basel). 5, 48-63 (2013).
Thiel, Kristina W., et al. "Delivery of chemo-sensitizing siRNAs to HER2+-breast cancer cells using RNA aptamers." Nucleic acids research 40.13 (2012): 6319-6337.
Uemura, N. et al. Helicobacter pylori infection and the development of gastric cancer. New England Journal of Medicine. 345, 784-789 (2001).
Wang, K. et al. BRCAA1 monoclonal antibody conjugated fluorescent magnetic nanoparticles for in vivo targeted magnetofluorescent imaging of gastric cancer. J Nanobiotechnol. 1, 9-23 (2011).
Wang, Z., Ruan, J., Cui, D.X. Advances and Prospect of Nanotechnology in Stem Cells. Nanoscale Resarch Letters. 4, 593-605 (2009).
Zhang, D. & Fan, D. New insights into the mechanisms of gastric cancer multidrug resistance and future perspectives. Future Oncol. 6, 527-537 (2010).
Zhang, H. et al. Crystal structure of 3WJ core revealing divalent ion-promoted thermostability and assembly of the Phi29 hexameric motor pRNA. RNA (New York, N. Y.). 19, 1226-1237 (2013).
Zhang, Y. X. et al. Identification of volatile biomarkers of gastric cancer cells and ultrasensitive electrochemical detection based on sensing interface of Au—Ag alloy coated MWCNTs. Theranostics. 4, 154-62 (2014).

(56) References Cited

OTHER PUBLICATIONS

Zhou, J., Shum, K. T., Burnett, J. C. & Rossi, J. J. Nanoparticle-Based Delivery of RNAi Therapeutics: Progress and Challenges. Pharmaceuticals (Basel, Switzerland). 6, 85-107 (2013).
Zhou, Z. J. et al. Folic acid-conjugated silica capped gold nanoclusters for targeted fluorescence/X-ray computed tomography imaging. Journal of Nanobiotechnology. 11, 17 (2013).

* cited by examiner

RNA NANOPARTICLE FOR TREATMENT OF GASTRIC CANCER

RELATED APPLICATIONS

This application is a § 371 National State Application of PCT/US2016/021444 filed Mar. 9, 2016 which claims the benefit of U.S. Provisional Patent Application No. 62/130,527, filed Mar. 9, 2015, the entire disclosure of which are hereby incorporated by reference in their entirety.

GOVERNMENT INTEREST

This invention was made with government support under CA151648 and EB012135 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Dec. 20, 2017, is named 2935720-006-US2 SL.txt and is 5,228 bytes in size.

TECHNICAL FIELD

The presently-disclosed subject matter relates to RNA nanostructure molecule and method to treat gastric cancer in a subject. More particularly, the presently disclosed subject matter relates to a RNA nanostructure and composition containing a multiple branched RNA nanoparticle, a gastric cancer targeting module, and an effective amount of a therapeutic agent. Further, the presently disclosed subject matter relates to a method of using the RNA nanoparticle composition to treat gastric cancer in a subject having or at risk of having gastric cancer.

INTRODUCTION

Gastric cancer is the one of the most common cancers, and the second leading cause of cancer-related death in the world (1,2). The effective treatment remains challenging primarily because most diagnosed patients present advanced stages of the disease. It remains very difficult to cure effectively, primarily because most patients present advanced stages of the diseases. Up to date, surgery, radiation and chemotherapies are generally very effective for early and in situ gastric cancers, but advanced and metastatic cases do not respond to chemo- or radiation therapies (3-5) and resistance to chemotherapy-induced apoptosis is a major cause for the failure of conventional therapies (6-8). The current prognosis of gastric cancer is very poor with 5-year survivals of less than 24% (9). Therefore, developing novel strategies and approaches for recognizing, tracking and killing gastric cancer cells in early disease stage is urgently demand.

Previously, multifunctional nanoprobes has been studies to realize targeted imaging and simultaneous therapy of gastric cancer (10,11). The previous studies show that subcutaneous and in situ gastric cancer tissues with 5 mm in diameter could be recognized and treated using multifunctional nanoprobes such as BRCAA1 (breast cancer associated antigen 1, AF208045) monoclonal antibody-conjugated fluorescent magnetic nanoparticles (12), Her2 monoclonal antibody-conjugated RNase-A-associated CdTe quantum dots (13), folic acid conjugated upper conversion nanoparticles (14), Folate conjugated gold nanorods (15), ce6-conjugated carbon dots (16), ce6-conjugated Au nanoclusters (Au NCs) (17,18). However, clinical translation of these prepared nanoprobes still presents great challenge because all these prepared nanoprobes are not only distributed to the site of gastric cancer, but also partially accumulated in other organs. Therefore, the development of safe and effective nanoprobes for in vivo targeted delivery, imaging and simultaneous therapy of early gastric cancer is desirable.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

The presently disclosed subject matter in some embodiments relates to an artificial RNA nanostructure molecule. The RNA nanostructure molecule includes a multiple branched RNA junction motif comprising at least one RNA oligonucleotides, and a gastric cancer targeting module conjugated to the RNA junction motif. In some embodiments, the RNA nanostructure further includes at least one bioactive agent. In some embodiments, the RNA nanostructure binds to gastric cancer cells. A non-limiting example of the bioactive agent is a therapeutic agent. In some embodiments, the bioactive agent includes drugs, fluorescent dyes, or chemicals. In some embodiments, the bioactive agent includes an imaging module. Non-limiting examples of the imaging module is fluorescent dye, including a non-limiting example Alexa647. In some embodiments, the diameter of the molecule is at least about 40 nm or less. In some embodiments, the molecule has zeta potential ranging from about −150 mV to about 150 mV. In some embodiments, the molecule has zeta potential ranging from about −125 my to about 75 mV. In some embodiments, the molecule is substantially stable in a pH value ranges from about 2 to about 13.

In some embodiments, the nanostructure comprises at least one chemical modification at 2' position. Non-limiting examples of the chemical modification includes 2'Fluoro, 2'Amine, and 2'O-Methyl. In some embodiments, the multiple branched RNA comprises sequence 5'-CCA-CAUAAAGGGCCCACUAuuCCCACAUACUUU-GUUGAUCC-3' (SEQ ID NO: 4). In some embodiments, the multiple branched RNA includes sequence 5'-UAGUGGGCCCUUUAUGUGG-3' (SEQ ID NO: 5).

In some embodiments, the multiple branched RNA junction motif is a three-branched RNA junction motif. In some embodiments of the present disclosure, the RNA molecules form dimers, trimers, hexamers, and patterned superstructures. Further, In some embodiments, a branch of the three-branched RNA junction motif includes an a3WJ RNA module (SEQ ID NO: 1); a b3WJ RNA module (SEQ ID NO: 2); or a c3WJ RNA module (SEQ ID NO: 3). In one embodiment, the three-branched RNA junction motif comprises an a3WJ RNA module (SEQ ID NO: 1); a b3WJ RNA module (SEQ ID NO: 2); and a c3WJ RNA module (SEQ ID NO: 3). The SEQ ID NO: 1 includes nucleotide sequence 5'-UUG CCA UGU GUA UGU GGG-3', the SEQ ID NO: 2 comprises nucleotide sequence 5'-CCC ACA UAC UUU GUU GAUCC-3', and the SEQ ID NO: 3 comprises nucleotide sequence 5'-GGA UCA AUC AUG GCA A-3'.

In some embodiments, the gastric cancer targeting module includes a ligand that binds to at least one gastric cancer cell surface marker. In some embodiments, the ligand binds to a folate receptor, an epidermal growth factor receptor 2 (ErbB-2/HER2), an epidermal growth factor receptor (EGFR), a HER2 or a combination thereof. In some embodiments, the ligand is an aptamer. Non-limiting examples of the aptamer are aptamers binding to EGFR, PDGFR, folate receptor, or a combination thereof. In one example, the ligand is a EGFR targeting aptamer. In one example, the ligand has sequence 5'-G CCU UAG UAA CGU GCU UUG AUG UCG AUU CGA CAG GAG GC 3' (SEQ ID NO: 6). In some embodiments, the targeting module is a folate. Non-limiting examples of folate are folic acid, 5-methyltetrahydro folate, 5-formyltetrahydrofolate, dihydrofolate, tetrahydrofolate, or a combination thereof.

In some embodiments, the bioactive agent is a drug, a fluorescent dye, a chemical, or a combination thereof. In some embodiments, wherein the bioactive agent is a siRNA, a miRNA, an anti-mRNA, a ribozyme RNAs, or an antisense RNAs. In some embodiments, the bioactive agent is directed a gastric cancer marker. In some embodiments, the bioactive agent is a siRNA sequence. Non-limiting examples of the siRNA are siRNA is directed to Survivin, Bcl-2, XIAP, BCL-XL, or BRCAA1. Non-limiting examples of the siRNA include siRNA sequence 5' GGACCACCGCAUCU-CUACAdTdT 3' (SEQ ID NO: 7), 5' dTdTCCUGGUG-GCGUAGAGAUGU 3' (SEQ ID NO: 8), 5'-AAGCUGu-CACAGAGGGGCUAC-3' (SEQ ID NO: 9), 5'GUAGCCCCUCUGUGACAGCUU-3 (SEQ ID NO: 10), 5'-CCAUGUGCUAUACAGUCAUUACUUU-3' (SEQ ID NO: 11), 5'-AAAGUAAUGACUGUAUAGCACAUGG-3' (SEQ ID NO: 12), 5'-UUGGACAAUGGACUGGUUGA-3' (SEQ ID NO: 13), or 5'-UCAACCAGUCCAUUGUC-CAA-3 (SEQ ID NO: 14). In one embodiment, siRNA is a BRCAA1 siRNA. A non-limiting example is a siRNA sequence 5'-CCACAUAAAGGGCCCACUA-3' (SEQ ID NO: 15). Another non-limiting example is a siRNA sequence 5'-UAGUGGGCCCUUUAUGUGG-3' (SEQ ID NO: 5). In some embodiments, the bioactive agent is a microRNA sequence. In some embodiments, the bioactive agent is an anti-miRNA molecule for a miRNA comprising miR-9, miR-10b, miR-21, or miR-26. In some embodiments, the bioactive agent is a miRNA molecule for a miRNA comprising let-7a, miR-10b, miR-25, miR-34a, miR-124, miR-145, or miR-181b.

Further provided, in some embodiments of the presently disclosed subject matter, is a composition including a therapeutically effective amount of the RNA nanostructure molecule as disclosed above and herein. In some embodiments, the composition further includes a pharmaceutically acceptable carrier.

Still further, the presently disclosed subject matter in some embodiments provides a nanoparticle delivery system including a RNA nanostructure molecule as disclosed above and herein. In some embodiments, the delivery system further includes a pharmaceutically acceptable carrier.

Yet further provided in some embodiments, is a method of treating gastric cancer in a subject having or at risk of having gastric cancer. The method includes the step of administering to the subject a therapeutically effective amount of a composition comprising the RNA nanostructure molecule as disclosed above and herein. In some embodiments, the method includes a composition further including a pharmaceutically acceptable carrier. In some embodiments, the subject is a mammal or a non-mammal vertebrate. In some embodiments, the subject is a human.

BRIEF DESCRIPTION OF THE DRAWINGS

FIG. 1A is the design of the RNA nanoparticles (SEQ ID NOS 1, 16, 3 and 4, respectively, in order of appearance). Left is the one use in animal trial. Right is the extended one to prepare the AFM images. FIG. 1B is the AFM image of extended 3WJ RNA nanoparticles. The RNA complex in left of a is estimated to be around 10 nm. Due to convolution of the tip size HO nm in diameter) in AFM images, features smaller than the size of the tip cannot be resolved. To characterize the structure of the RNA constructs, the 3WJ nanoparticles were extended by 39-60 base-pairs (in red color), which is within the persistence length of dsRNA and will not affect the 3WJ folding as described before (31), to generate the AFM image as shown.

FIG. 7A is an image showing 0 day at un-treated mouse; FIG. 7B is an image showing 0 day in un-treated mouse; FIG. 7C shows 14 days at control mouse; FIG. 7D is an image showing 14 days in test mouse, and FIG. 7E shows tumor tissues from experiment.

FIG. 13A is a graphs illustrating the effects of pH (pH 2 to 13) on the fluorescent intensity of RNA nanoparticles by PerkinElmer LS 55 spectrofluorimeter, and FIG. 13B is an image showing the effects of pH (pH 2 to 13) on the stability of RNA nanoparticles examined by 1.2% agarose gel electrophoresis.

DESCRIPTION OF EXEMPLARY EMBODIMENTS

Figure 1:
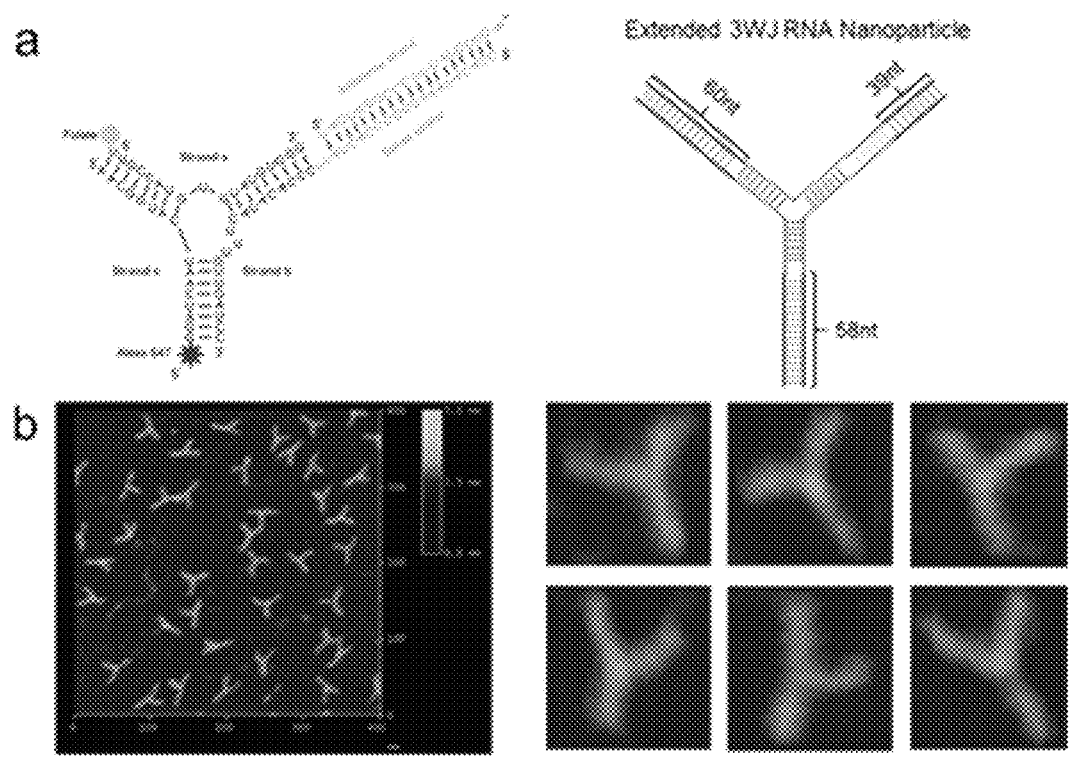
FIGS. 1A and 1B include diagrams and images illustrating the global structure of the therapeutic RNA nanoparticles with BRCAA1 siRNA.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom.

In certain instances, nucleotides and polypeptides disclosed herein are included in publicly-available databases, such as GENBANK® and SWISSPROT. Information including sequences and other information related to such nucleotides and polypeptides included in such publicly-available databases are expressly incorporated by reference. Unless otherwise indicated or apparent the references to such publicly-available databases are references to the most recent version of the database as of the filing date of this Application.

While the terms used herein are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method. As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

The presently disclosed subject matter in some embodiments relates to an artificial RNA nanostructure molecule. The RNA nanostructure molecule includes a multiple branched RNA junction motif comprising at least one RNA oligonucleotides, and a gastric cancer targeting module conjugated to the RNA junction motif. In some embodiments, the RNA oligonucleotides is at least 6 nucleotides in length. In some embodiments, the RNA nanostructure further includes at least one bioactive agent. In some embodiments, the RNA nanostructure binds to gastric cancer cells. A non-limiting example of the bioactive agent is a therapeutic agent. In some embodiments, the bioactive agent includes drugs, fluorescent dyes, or chemicals. In some embodiments, the bioactive agent includes an imaging module. Non-limiting examples of the imaging module is fluorescent dye, including a non-limiting example Alexa647. In some embodiments, the nanostructure comprises at least one chemical modification at 2' position. Non-limiting examples of the chemical modification includes 2'Fluoro, 2'Amine, and 2'O-Methyl. In some embodiments, the multiple branched RNA comprises sequence 5'-CCA-CAUAAAGGGCCCACUAuuCCCACAUACUUU-GUUGAUCC-3' (SEQ ID NO: 4). In some embodiments, the multiple branched RNA includes sequence 5'-UAGUGGGCCCUUUAUGUGG-3' (SEQ ID NO: 5).

The term "RNA" refers to a molecule comprising at least one ribonucleotide residue. By "ribonucleotide" is meant a nucleotide with a hydroxyl group at the 2' position of a β-D-ribofuranose moiety. The terms encompass double stranded RNA, single stranded RNA, RNAs with both double stranded and single stranded regions, isolated RNA such as partially purified RNA, essentially pure RNA, synthetic RNA, recombinantly produced RNA, as well as altered RNA, or analog RNA, that differs from naturally occurring RNA by the addition, deletion, substitution, and/or alteration of one or more nucleotides. Such alterations can include addition of non-nucleotide material, such as to the end(s) of an siRNA or internally, for example at one or more nucleotides of the RNA. Nucleotides in the RNA molecules of the presently disclosed subject matter can also comprise non-standard nucleotides, such as non-naturally occurring nucleotides or chemically synthesized nucleotides or deoxynucleotides. These altered RNAs can be referred to as analogs or analogs of a naturally occurring RNA.

As disclosed herein, RNA nanotechnology has recently emerged as an important field due to recent finding of its high thermodynamic stability, favorable and distinctive in vivo attributes (US 2014/0179758, hereby incorporate by reference in its entirety). In some embodiments of the present disclosure, as disclosed in US2014/0179758, the RNA molecules form dimers, trimers, hexamers, and patterned superstructures. Further, RNA nanoparticles can be fabricated with precise control of shape, size and stoichiometry, as demonstrated by the packaging RNA (pRNA) of the bacteriophage phi29 DNA packaging motor, which forms dimmers, trimers, and hexamers via hand-in-hand interactions of the interlocking loops (27,28). The pRNA contains an ultra-stable three-way junction (3WJ) motif (29-31), which can be assembled from three short fragments with extremely high affinity. Recently, the crystal structure of the pRNA-3WJ motif was obtained (32) and a variety of therapeutic RNA nanoparticles using the pRNA-3WJ and pRNA-X motifs as scaffolds have been constructed (33-34). The pRNA-3WJ nanoparticles display thermodynamically stable properties, including high melting temperature with low free energy, resistance to denaturation in 8M urea, and resistance to dissociation at very low concentrations in the blood. Boiling resistant RNA nanoparticles with controllable shapes and defined stoichiometry have recently been reported (36). Various imaging groups, such as fluorophores; targeting ligands, such as receptor binding aptamers; and therapeutic modules, such as siRNA, miRNA or ribozymes can be integrated into the 3WJ scaffold without affecting the folding and functionality of the core motif and incorporated functional moieties. Upon 2'-Fluoro (2'-F) modifications of Uracil (U) and Cytosine (C) nucleotides, the RNA nanoparticles become resistant to RNase degradation with enhanced in vivo half-life while retaining authentic functions of the incorporated modules. Furthermore, the pRNA nanoparticles are non-toxic, non-immunogenic, and display favorable biodistribution and pharmacokinetic profiles in mice.

In some embodiments, the multiple branched RNA junction motif is a three-branched RNA junction motif. In some embodiments of the present disclosure, the RNA molecules form dimers, trimers, hexamers, and patterned superstructures. Further, In some embodiments, a branch of the three-branched RNA junction motif includes an a3WJ RNA module (SEQ ID NO: 1); a b3WJ RNA module (SEQ ID NO: 2); or a c3WJ RNA module (SEQ ID NO: 3). In one embodiment, the three-branched RNA junction motif comprises an a3WJ RNA module (SEQ ID NO: 1); a b3WJ RNA module (SEQ ID NO: 2); and a c3WJ RNA module (SEQ ID NO: 3). The SEQ ID NO: 1 includes nucleotide sequence 5'-UUG CCA UGU GUA UGU GGG-3', the SEQ ID NO: 2 comprises nucleotide sequence 5'-CCC ACA UAC UUU GUU GAUCC-3', and the SEQ ID NO: 3 comprises nucleotide sequence 5'-GGA UCA AUC AUG GCA A-3'.

In some embodiments, the diameter of the molecule is at least about 40 nm or less. The diameter is at least about 35 nm or less, at least about 30 nm or less, at least about 25 nm or less, at least 20 nm or less, at least 15 nm or less, at least 10 nm or less, at least 5 nm or less.

In some embodiments, the molecule has zeta potential ranging from about −150 mV to about 150 mV. The RNA molecule has a zeta potential ranging from about −140 mV to about 140 mV, from about −130 mV to about 130 mV, from about −120 mV to about 120 mV, from about −110 mV to about 110 mV, from about −100 mV to about 100 mV, from about −90 to about 90 mV, form about −80 mV to about 80 mV, from about −70 mV to about 70 mV, from about −60 mV to about 60 mV, from about −50 mV to about 50 mV. The molecule has a zeta potential ranging from about −40 my to about 40 mV, from about −30 mV to about 30 mV, from about −20 mV to about 20 mV, from about −10 mV to about 10 mV.

In some embodiments, the molecule is substantially stable in a pH value ranges from about 2 to about 13. The RNA molecule is substantially stable in pH about 2, 3, 4, 5, 6, 7, 8, 9, 10, 11, 12 and 13. As used herein, the term "substantially stable" can refer to physical and/or chemical stability. As will be recognized by those of ordinary skill in the art, the term "substantially stable" can refer to stability of the composition under certain conditions, relative to an initial composition (i.e., when a particular batch of the composition is initially prepared). In this regard, as will be recognized by those of ordinary skill in the art, one manner in which stability of a particular embodiment of the composition can be determined is as follows: preparing a batch of the embodiment of the composition, making an initial assessment of a sample of the composition (control sample), subjecting a sample of the composition to conditions of interest (e.g., storage at a particular temperature for a particular time period) (test sample), making an assessment of the test sample, and comparing the assessment of the control sample to the assessment of the test sample. Calculations can be made to determine whether the amounts present in the test sample are 100%±20, 19, 18, 17, 16, 15, 14, 13, 12, 11, 10, 9, 8, 7, 6, 5, 4, 3, 2, 1, 0.5, or 0.1% of the amount that is in the control sample.

In some embodiments, the RNA nanostructure includes a gastric cancer targeting module. In some embodiments, the gastric cancer targeting module includes a ligand that binds to at least one gastric cancer cell surface marker. In some embodiments, the ligand binds to a folate receptor, an epidermal growth factor receptor 2 (ErbB-2/HER2), an epidermal growth factor receptor (EGFR), a HER2 or a combination thereof. In some embodiments, the ligand is an aptamer. The term "aptamer" as used herein refers to an oligonucleotide that can bind specifically to its target with high affinity. Non-limiting examples of the aptamer are aptamers binding to EGFR, PDGFR, folate receptor, or a combination thereof. In one example, the ligand is a EGFR targeting aptamer. In one example, the ligand has sequence 5'-G CCU UAG UAA CGU GCU UUG AUG UCG AUU CGA CAG GAG GC 3' (SEQ ID NO: 6). In some embodiments, the targeting module is a folate.

The term "folate" as used herein can comprise a genus of well-defined B-vitamin compounds, including but not limited to, 5-methyltetrahydro folate, 5-formyltetrahydrofolate, dihydrofolate, tetrahydrofolate, folic acid and other folate compounds. As disclosed herein, the targeted delivery systems call for a ligand-receptor pair that is specifically found in cancer cells. Many, but not all, cancer cells, including stomach, ovary, lung, breast, kidney, endometrium, colon and hematopoietic cells, over-expressed folate receptors (FRs) than normal cells for high uptake of folate, since folate is essential component during DNA replication and methylation in highly proliferating cells. Folic acid (FA), a synthetic oxidized form of folate, has been widely used as a ligand conjugate in various cancer targeting materials.

In some embodiments, the bioactive agent is a drug, a fluorescent dye, a chemical, or a combination thereof. In some embodiments, wherein the bioactive agent is a siRNA, a miRNA, an anti-mRNA, a ribozyme RNAs, or an antisense RNAs. In some embodiments, the bioactive agent is directed a gastric cancer marker. In some embodiments, the bioactive agent is a siRNA sequence. Non-limiting examples of the siRNA are siRNA is directed to Survivin, Bcl-2, XIAP, BCL-XL, or BRCAA1.

In some embodiments of the present disclosure, a RNA nanotechnology approach is adopted to overcome some of the aforementioned challenges, and report the strategy to target and deliver therapeutic BRCAA1 siRNA to in vivo stomach cancer tissues using FA-conjugated pRNA-3WJ nanoparticles. The present disclosure relates to the construction of multi-functional, thermodynamically and chemically stable RNA nanoparticles harboring sequences that allow specific binding to stomach cancer specific cell surface antigens or receptors resulting in the internalization of RNA nanoparticles into target cells and delivery of the siRNA, miRNA, and drugs for attaining synergistic effects for the treatment of stomach cancer. Further, the present disclosure relates to effects of prepared RNA nanoparticles on the regression of gastric cancer tissues in vivo, and potential molecular mechanism.

It has been proposed for long time that the RNAi can be applied for potential cancer treatment strategy. However, lacking of effect delivery system, the therapeutic small RNAs including siRNAs, miRNAs, anti-sense RNAs, etc., remain undrugable. The RNA nanoparticle-based nano-delivery platform can overcome aforementioned limitations for conventional cancer therapeutic and opens new opportunities for specific delivering RNAi therapeutics to gastric cancer without damaging healthy organs and tissues, reducing the toxicity and side effects, improving the therapeutic effects, and exhibiting great potential in clinical cancer therapy.

The phrase "gastric cancer marker" as used herein refers to genes or gene products (e.g., RNA molecules or proteins) which are characteristic of some or all of the cells in gastric cancer. A gastric cancer marker with diagnostic value can be a gene or gene product expressed in normal, non-cancerous cells, but is characteristic of a type or classification of cancer by, for example, its over-expression or under-expression as compared to its expression in normal, non-cancerous cells. A gastric cancer marker with prognostic value is a gene or gene product for which the over-expression or under-expression confers predictive information about the future aggressiveness of a cancer and/or its response to therapy at the time of diagnosis. In a cancer sample, the patterns of expression of diagnostic and prognostic cancer markers allow one to accurately identify and determine the future course of the disease, respectively. Non-limiting examples of gastric cancer biomarkers are described in WO2012167112 (herein incorporated by reference in its entirety).

The terms "small interfering RNA", "short interfering RNA", "small hairpin RNA", "siRNA", and shRNA are used interchangeably and refer to any nucleic acid molecule capable of mediating RNA interference (RNAi) or gene silencing. See e.g., Bass, Nature 411:428-429, 2001; Elbashir et al., Nature 411:494-498, 2001a; and PCT International Publication Nos. WO 00/44895, WO 01/36646, WO 99/32619, WO 00/01846, WO 01/29058, WO 99/07409, and WO 00/44914. In one embodiment, the siRNA comprises a double stranded polynucleotide molecule comprising complementary sense and antisense regions, wherein the antisense region comprises a sequence complementary to a region of a target nucleic acid molecule (for example, a nucleic acid molecule encoding Survivin). In another embodiment, the siRNA comprises a single stranded polynucleotide having self-complementary sense and antisense regions, wherein the antisense region comprises a sequence complementary to a region of a target nucleic acid molecule. In another embodiment, the siRNA comprises a single stranded polynucleotide having one or more loop structures and a stem comprising self complementary sense and antisense regions, wherein the antisense region comprises a sequence complementary to a region of a target nucleic acid molecule, and wherein the polynucleotide can be processed either in vivo or in vitro to generate an active siRNA capable of mediating RNAi. As used herein, siRNA molecules need not be limited to those molecules containing only RNA, but further encompass chemically modified nucleotides and non-nucleotides.

In some embodiments, the presently disclosed subject matter takes advantage of the ability of short, double stranded RNA molecules to cause the down regulation of cellular genes, a process referred to as RNA interference. As used herein, "RNA interference" (RNAi) refers to a process of sequence-specific post-transcriptional gene silencing mediated by a small interfering RNA (siRNA). See Fire et al., Nature 391:806-811, 1998 and U.S. Pat. No. 6,506,559, each of which is incorporated by reference herein in its entirety. The process of post-transcriptional gene silencing is thought to be an evolutionarily conserved cellular defense mechanism that has evolved to prevent the expression of foreign genes (Fire, Trends Genet 15:358-363, 1999).

Disclosed herein are examples of siRNA including Survivin-specific, Bcl-2, XIAP, and BCL-XL siRNA sequences. The Survivin-specific siRNA includes sense sequence: 5' GGACCACCGCAUCUCUACAdTdT 3' (SEQ ID NO: 7) and antisense sequence: 5' dTdTCCUGGUGGCGUAGA-GAUGU 3' (SEQ ID NO: 8) (See, e.g., Cancer Gene Ther. 2004 March; 11(3):186-93. Knockdown of survivin expression by small interfering RNA reduces the clonogenic survival of human sarcoma cell lines independently of p53.); the Bcl-2 siRNA includes sense sequence: 5'-AAGCUGu-CACAGAGGGGCUAC-3' (SEQ ID NO: 9), and antisense sequence: 5'-GUAGCCCUCUGUGACAGCUU-3 (SEQ ID NO: 10) (See, e.g., *Nucleic Acids Res.* 2012 July; 40(13):6319-37. doi: 10.1093/nar/gks294. Epub 2012 Mar. 30. Delivery of chemo-sensitizing siRNAs to HER2+-breast cancer cells using RNA aptamers.); XIAP siRNA includes sense sequence: 5'-CCAUGUGCUAUACAGUCAUUAC-UUU-3' (SEQ ID NO: 11), and antisense sequence: 5'-AAAGUAAUGACUGUAUAGCACAUGG-3' (SEQ ID NO: 12) (See, e.g., *Mol Cancer.* 2006 Sep. 5; 5:34. Specific down-regulation of XIAP with RNA interference enhances the sensitivity of canine tumor cell-lines to TRAIL and doxorubicin); and BCL-XL siRNA includes sense sequence: 5'-UUGGACAAUGGACUGGUUGA-3 (SEQ ID NO: 13), antisense sequence: 5'-UCAACCAGUCCAUUGUCCAA-3 (SEQ ID NO: 14) (See, e.g., *Acta Biochim Biophys Sin* (Shanghai). 2005 August; 37(8):555-60. Silencing of Bcl-XL expression in human MGC-803 gastric cancer cells by siRNA.) Further, in one embodiment, siRNA is a BRCAA1 siRNA. A non-limiting example is a siRNA sequence 5'-CCACAUAAAGGGCCCACUA-3' (SEQ ID NO: 15). Another non-limiting example is a siRNA sequence 5'-UAGUGGGCCCUUUAUGUGG-3' (SEQ ID NO: 5).

In some embodiments, the bioactive agent is a microRNA sequence. The term "MicroRNAs (miRNAs)" as used herein are single-stranded, or double stranded non-coding RNAs, at least about 6 nucleotide in length that can regulate gene expression at the post-transcriptional level by either degrading their target mRNAs or inhibiting their translation (1,2). MiRNAs play important roles in regulating cell cycle, proliferation, differentiation, metabolism, and apoptosis (1). A compendium of microRNA and respective microRNA binding sequences is available at the miRNA registry. (See, e.g., Griffiths-Jones et al. (2006) Nucl. Acids Res. 34:D140-D144; US20140045709, herein incorporate by reference in their entireties.) In particular embodiments, the microRNA and microRNA binding sequence employed in the present assay are associated with a disease or condition, wherein an antagonist or agonist to the microRNA would be useful in preventing or treating the disease or condition.

In some embodiments, the present disclosure provides inhibitors of miRNAs (e.g., anti-miR-21). Compositions comprising such inhibitors and methods for inhibiting miR-21 using such inhibitors are also disclosed herein. Any miRNA inhibitor may be used alone, or with other miRNA inhibitor(s) known in the art. In some embodiments, the miRNA inhibitor comprises an antisense molecule. In some embodiments, the antisense molecule could be a single or a double stranded sequence. Examples of antisense molecule include, but are not limited to, siRNAs, triple-helix-forming agents, ribozymes, RNAi, synthetic peptide nucleic acids (PNAs), antigenes (agRNAs), LNA/DNA copolymers, small molecule chemical compounds, and antisense oligonucleotides.

In some embodiments, the microRNA sequence is at least 6 nucleotide in length. In some embodiments, the miRNA molecule or an equivalent, or a mimic thereof is from about 6 to about 30 nucleotides in length. In some embodiments, the miRNA is about 12 to about 30 nucleotides in length. In some embodiments, the miRNA is from about 15 to about 28 nucleotides in length. In some embodiments, the miRNA is about 19 to about 25 nucleotides in length. In some embodiments, the miRNA molecule has a length of at least about 6, 7, 8, 9, 10, 11, 12, 13, 14, 15, 16, 17, 18, 19, 20, 21, 22, 23, 24, 25, 26, 27, 28, 29, about 30 nucleotides or more. In some embodiments, an antagomir of a miRNA molecule is from about 6 to about 30 nucleotides in length, from about 10 to about 30 nucleotides in length, from about 12 to about 28 nucleotides in length. In some embodiments, the antagomir of a miRNA molecule has a length of at least about 6, 7, 8, 9, 10, 11, 12, 13, 14, 15, 16, 17, 18, 19, 20, 21, 22, 23, 24, 25, 26, 27, 28, 29, about 30 nucleotides or more.

In some embodiments, the miRNA interferes oncogenic miRNA to regress cancer growth. The RNA nanostructure molecule contains anti-miRNA that silences oncogenic miRNAs, including but not limited to, miR-9, miR-10b, miR-21, miR-17, and miR-26. In some embodiments, the miRNA rescues down-regulated cancer suppressive miRNAs, where the RNA nanostructure introduces cancer suppressive miRNAs, including but not limited to, let-7a, miR-10b, miR-25, miR-34a, miR-124, miR-145, and miR-181b. Further examples is disclosed in US20140045709, which herein incorporate by reference in its entirety.

The presently disclosed subject matter further provide a composition including a therapeutically effective amount of the RNA nanostructure molecule as disclosed above and herein. In some embodiments, the composition further includes a pharmaceutically acceptable carrier.

The presently disclosed subject matter in some embodiments provides a nanoparticle delivery system including a RNA nanostructure molecule as disclosed above and herein. In some embodiments, the delivery system further includes a pharmaceutically acceptable carrier.

The term "pharmaceutically acceptable carrier" as used herein refers to a diluent, adjuvant, excipient, or vehicle with which a heterodimeric probe of the disclosure is administered and which is approved by a regulatory agency of the federal or a state government or listed in the U.S. Pharmacopeia or other generally recognized pharmacopeia for use in animals, and more particularly in humans. Such pharmaceutical carriers can be liquids, such as water and oils, including those of petroleum, animal, vegetable, or synthetic origin, such as peanut oil, soybean oil, mineral oil, sesame oil, and the like. The pharmaceutical carriers can be saline, gum acacia, gelatin, starch paste, talc, keratin, colloidal silica, urea, and the like. When administered to a patient, the heterodimeric probe and pharmaceutically acceptable carriers can be sterile. Water is a useful carrier when the heterodimeric probe is administered intravenously. Saline solutions and aqueous dextrose and glycerol solutions can also be employed as liquid carriers, particularly for injectable solutions. Suitable pharmaceutical carriers also include excipients such as glucose, lactose, sucrose, glycerol monostearate, sodium chloride, glycerol, propylene, glycol, water, ethanol, and the like. The present compositions, if desired, can also contain minor amounts of wetting or emulsifying agents, or pH buffering agents. The present compositions advantageously may take the form of solutions, emulsion, sustained release formulations, or any other form suitable for use.

The term "therapeutically effective amount," as used herein, refers to the amount of a composition containing administered to a patient already suffering from a disease, condition, or disorder, sufficient to cure or at least partially arrest, or relieve to some extent one or more of the symptoms of the disease, disorder, or condition being treated. The effectiveness of such compositions depend upon conditions including, but not limited to, the severity and course of the disease, disorder, or condition, previous therapy, the patient's health status and response to the drugs, and the judgment of the treating physician. By way of example only, therapeutically effective amounts may be determined by routine experimentation, including but not limited to a dose escalation clinical trial.

The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

Suitable methods for administering to a subject an effective amount of the composition in accordance with the methods of the present disclosure include but are not limited to systemic administration, parenteral administration (including intravascular, intramuscular, intraarterial administration), oral delivery, buccal delivery, subcutaneous administration, inhalation, intratracheal installation, surgical implantation, transdermal delivery, local injection, and hyper-velocity injection/bombardment. Where applicable, continuous infusion can enhance drug accumulation at a target site (see, e.g., U.S. Pat. No. 6,180,082).

In some embodiments, the present disclosure provides a method of treating gastric cancer in a subject having or at risk of having gastric cancer. The method includes the step of administering to the subject a therapeutically effective amount of a composition comprising the RNA nanostructure molecule as disclosed above and herein. In some embodiments, the method includes a composition further including a pharmaceutically acceptable carrier. In some embodiments, the subject is a mammal or a non-mammal vertebrate. In some embodiments, the subject is a human. More specifically, in the method, the RNA nanostructure molecule includes a multiple branched RNA junction motif comprising at least one RNA oligonucleotides, and a gastric cancer targeting module conjugated to the RNA junction motif. In some embodiments of the method, the RNA nanostructure further includes at least one bioactive agent. The RNA nanostructure binds to gastric cancer cells. A non-limiting example of the bioactive agent is a therapeutic agent. The bioactive agent includes drugs, fluorescent dyes, or chemicals. In some embodiments, the bioactive agent includes an imaging module. In some embodiment of the method, the diameter of the RNA molecule is at least about 40 nm or less, the molecule has zeta potential ranging from about −150 mV to about 150 mV, and the molecule is substantially stable in a pH value ranges from about 2 to about 13. In some embodiments of the method, the nanostructure comprises at least one chemical modification at 2' position. Non-limiting examples of the chemical modification includes 2'Fluoro, 2'Amine, and 2'O-Methyl. In some embodiments, the multiple branched RNA comprises sequence 5'-CCACAUAAAGGGCCCACUAuuCCCACAUACUUU-GUUGAUCC-3' (SEQ ID NO: 4). In some embodiments, the multiple branched RNA includes sequence 5'-UAGUGGGCCCUUUAUGUGG-3' (SEQ ID NO: 5). In further embodiments, the multiple branched RNA junction motif is a three-branched RNA junction motif. In some embodiments of the present disclosure, the RNA molecules form dimers, trimers, hexamers, and patterned superstructures. Further, In some embodiments, a branch of the three-branched RNA junction motif includes an a3WJ RNA module (SEQ ID NO: 1); a b3WJ RNA module (SEQ ID NO: 2); or a c3WJ RNA module (SEQ ID NO: 3). In one embodiment, the three-branched RNA junction motif comprises an a3WJ RNA module (SEQ ID NO: 1); a b3WJ RNA module (SEQ ID NO: 2); and a c3WJ RNA module (SEQ ID NO: 3). The SEQ ID NO: 1 includes nucleotide sequence 5'-UUG CCA UGU GUA UGU GGG-3', the SEQ ID NO: 2 comprises nucleotide sequence 5'-CCC ACA UAC UUU GUU GAUCC-3', and the SEQ ID NO: 3 comprises nucleotide sequence 5'-GGA UCA AUC AUG GCA A-3'.

Further, the gastric cancer targeting module includes a ligand that binds to at least one gastric cancer cell surface marker. In some embodiments, the ligand binds to a folate receptor, an epidermal growth factor receptor 2 (ErbB-2/HER2), an epidermal growth factor receptor (EGFR), a HER2 or a combination thereof. In some embodiments, the ligand is an aptamer. Non-limiting examples of the aptamer are aptamers binding to EGFR, PDGFR, folate receptor, or a combination thereof. In one example, the ligand is a EGFR targeting aptamer. In one example, the ligand has sequence 5'-G CCU UAG UAA CGU GCU UUG AUG UCG AUU CGA CAG GAG GC-3' (SEQ ID NO: 6). In some embodiments, the targeting module is a folate. Non-limiting examples of folate are folic acid, 5-methyltetrahydro folate, 5-formyltetrahydrofolate, dihydrofolate, tetrahydrofolate, or a combination thereof.

The RNA nanostructure of the method further includes at least one bioactive agent. The bioactive agent is a drug, a fluorescent dye, a chemical, or a combination thereof. Further, the bioactive agent includes a siRNA, a miRNA, an anti-mRNA, a ribozyme RNAs, or an antisense RNAs. In some embodiments, the bioactive agent is directed a gastric cancer marker. In some embodiments, the bioactive agent is a siRNA sequence. Non-limiting examples of the siRNA are siRNA is directed to Survivin, Bcl-2, XIAP, BCL-XL, or BRCAA1. Non-limiting examples of the siRNA include siRNA sequence 5' GGACCACCGCAUCUCUACAdTdT 3' (SEQ ID NO: 7), 5' dTdTCCUGGUGGCGUAGA-GAUGU 3' (SEQ ID NO: 8), 5'-AAGCUGuCACA-GAGGGGCUAC-3' (SEQ ID NO: 9), 5'GUAGCCCCUCU-GUGACAGCUU-3 (SEQ ID NO: 10), 5'-CCAUGUGCUAUACAGUCAUUACUUU-3' (SEQ ID NO: 11), 5'-AAAGUAAUGACUGUAUAGCACAUGG-3' (SEQ ID NO: 12), 5'-UUGGACAAUGGACUGGUUGA-3' (SEQ ID NO: 13), or 5'-UCAACCAGUCCAUUGUC-CAA-3 (SEQ ID NO: 14). In one embodiment, siRNA is a BRCAA1 siRNA. A non-limiting example is a siRNA sequence 5'-CCACAUAAAGGGCCCACUA-3' (SEQ ID NO: 15). Another non-limiting example is a siRNA sequence 5'-UAGUGGGCCCUUUAUGUGG-3' (SEQ ID NO: 5). In some embodiments, the bioactive agent is a microRNA sequence. In some embodiments, the bioactive agent is an anti-miRNA molecule for a miRNA comprising miR-9, miR-10b, miR-21, or miR-26. In some embodiments, the bioactive agent is a miRNA molecule for a miRNA comprising let-7a, miR-10b, miR-25, miR-34a, miR-124, miR-145, or miR-181b.

As used herein, the term "subject" refers to a target of administration of the pharmaceutical composition. The subject of the herein disclosed methods can be a vertebrate, such as a mammal, a fish, a bird, a reptile, or an amphibian. Thus, the subject of the herein disclosed methods can be a human or non-human. Thus, veterinary therapeutic uses are provided in accordance with the presently disclosed subject matter. As such, the presently disclosed subject matter provides for administration to mammals such as humans and non-human primates, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; rabbits, guinea pigs, and rodents. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like. The term does not denote a particular age or sex.

Further, in some embodiments, the RNA nanoparticle based nano-delivery platform is expected to outperform treatment strategies for gastric cancer therapy in several aspects: (1) RNA nanoparticles have defined size, structure and stoichiometry. Unpredictable side effects arising from heterogeneous particles can thus be avoided. (2) Nanoscaled size of the RNA nanoparticles facilitates tissue penetration and target to tumor. (3) RNA nanoparticles are easy to construct by self-assembly, highly soluble and not prone to aggregation. (4) The RNA nanoparticles are thermodynamically stable and, therefore, the entire construct will remain intact at ultra-low concentrations in the body. (5) The polyvalent nature of the RNA nanoparticle allows for easy integration of targeting modules, imaging modules and therapeutic modules into a single form. (6) RNA nanoparticles display low or no immunogenicity and/or toxicity even at high doses. The 3WJ-pRNA scaffold displays favorable pharmacokinetic and pharmacodynamic profiles in vivo (half-life of 5-10 hours compared to 0.25-0.75 hours of the most stable 2'F modified siRNA counterparts); non-toxic; and no induction of interferon or cytokines.

The presently disclosed subject matter is further illustrated by the following specific but non-limiting examples. The following examples may include compilations of data that are representative of data gathered at various times during the course of development and experimentation related to the present disclosure.

EXAMPLES

This study reports the use of the thermostable three-way junction (3WJ) of bacteriophage phi29 motor pRNA to escort folic acid, a NIR image marker and BRCAA1 siRNA for targeting, imaging, delivery, gene silencing and regression of gastric cancer in animal models. In vitro assay revealed that the RNA nanoparticles specifically bind to gastric cancer cells, and knock-down the BRCAA1 gene. Apoptosis of gastric cancer cells was observed. Animal trials confirmed that these RNA nanoparticles could be used to image gastric cancer in vivo, while showing little accumulation in crucial organs and tissues. The volume of gastric tumors noticeably decreased during the course of treatment. No damage to important organs by RNA nanoparticles was detectible. All the results indicated that this novel RNA nanotechnology can overcome conventional cancer therapeutic limitations and opens new opportunities for specific delivery of therapeutics to stomach cancer without damaging normal cells and tissues, reduce the toxicity and side effect, improve the therapeutic effect, and exhibit great potential in clinical tumor therapy.

Materials and Methods

Construction and Characterization of FA Conjugated BRCAA1-siRNA pRNA-3WJ nNnoparticles The pRNA-3WJ nanoparticle consisted of three fragments, $a_{3WJ}$, $b_{3WJ}$ and $c_{3WJ}$, was functionalized with folate, as targeting ligand; Alexa$_{647}$, as imaging module; and BRCAA1 siRNA (or scrambled control), as therapeutic module. The RNA fragments were then synthesized chemically (TriLink), self-assembled into RNA nanoparticles, and characterized by 1.2% agarose gel shift assays and AFM imaging as well as Zeta potential/Particle Sizer, as described previously (52). The construct contains sequences as following:

```
Strand 1:
                                         (SEQ ID NO: 1)
5' (folate)UUGCCAUGUGUAUGUGGG 3';

Strand 2:
                                         (SEQ ID NO: 4)
5' CCACAUAAAGGGCCCACUAuuCCCACAUACUUUGUUGAUCC 3'

Strand 3:
                                         (SEQ ID NO: 3)
5' (Alexa 647)GGAUCAAUCAUGGCAA 3'

Strand 4:
                                         (SEQ ID NO: 16)
5' UAGUGGGCCCUUUAUGUGGuu 3'
```

In order to evaluate the effects of a wide pH range on the stability of RNA nanoparticles, the prepared RNA nanoparticles were dispersed in varied pH buffers for 12 h, RNA nanoparticles/buffer=1:1(v/v), and pH ranged from 2 to 13 (Table 1: details of preparation of a series of buffer solutions), then 1.2% agarose gel electrophoresis was used to characterize the stability of prepared RNA nanoparticles. Effects of pH on the fluorescent intensity of RNA nanoparticles were investigated by measuring the fluorescent intensity of RNA samples with different pH via the photoluminescence (PL) spectra (Perkin Elmer LS55 spectrofluorimeter).

TABLE 1

Preparation for a series of buffer solutions (pH 2 to 13)

| pH | 0.2M glycine (ml) | 0.2M HCl (ml) | Deionized water (ml) |
|---|---|---|---|
| 2* | 5 | 4.4 | 10.6 |
| 3* | 5 | 1.14 | 13.86 |

| | 0.2M Na$_2$HPO$_4$ (ml) | 0.1M Citrate (ml) | |
|---|---|---|---|
| 4$^\Delta$ | 7.71 | 12.29 | / |
| 5$^\Delta$ | 10.3 | 9.7 | / |
| 6$^\Delta$ | 12.63 | 7.37 | / |
| 7$^\Delta$ | 16.47 | 3.53 | / |
| 8$^\Delta$ | 19.15 | 0.85 | / |

| | 0.2M glycine | 0.2M NaOH | |
|---|---|---|---|
| 9▲ | 5 | 0.88 | 14.12 |
| 10▲ | 5 | 3.2 | 11.8 |

| | 0.1M Na$_2$CO$_3$(ml) | 0.1M NaHCO$_3$(ml) | |
|---|---|---|---|
| 11★ | 19 | 1 | / |

TABLE 1-continued

Preparation for a series of buffer solutions (pH 2 to 13)

| | 0.05M Na$_2$HPO$_4$ (ml) | 0.1M NaOH (ml) | |
|---|---|---|---|
| 12☆ | 10 | 5.38 | 4.62 |
| | 0.2M KCl | 0.2M NaOH | |
| 13● | 5 | 13.2 | 1.8 |

*Glycine HCl buffer
ΔPhosphate Citrate buffer
▲Glycine NaOH buffer
★Crabonate Bicarbonate buffer
☆Phosphate NaOH buffer
●KCl NaOH buffer The RNA nanoparticles contained 2'-F modified U and C nucleotides to make them resistant to RNase degradation. However, Effects of RNAase A on the stability of RNA nanoparticles was still investigated. RNase A-free purified water was used to dilute RNAse A (Sigma Company), the resulting solutions were respectively exhibited different concentration of RNAse A (10 U, 50 U, 100 U, 500 U, 1000 U, 10000 U), then, each tube was respectively added into 1 µg RNA nanoparticles, incubated at 37° C. for 12 h, then 10% SDS-PAGE (sodium dodecylsulfate-polyacrylamide gel electrophoresis) gel electrophoresis is used to observe effects of RNAse A on the stability of RNA nanoparticles. The pRNA-3WJ was prepared by diluting 100 µM of the complexes in diethylpyrocarbonate (DEPC) treated water with PBS at 1:1 (v/v) right before the experiments.

Effects of Prepared RNA Nanoparticles on Cell Binding Efficiency and Specificity The human gastric cancer MGC803 cells and human gastric epithelial GES-1 cells (Cell Bank of Type Culture Collection of Chinese Academy of Sciences) were maintained at 37° C. (5% CO$_2$) in Dulbecco's Modified Eagle's Medium (DMEM, HyClone) supplemented with 10% (v/v) fetal bovine serum (Gibco), 100 U/mL penicillin, and 1 mg/mL streptomycin. Cell culture products and reagents were purchased from GIBCO. 200 nM AlexaFluor647 labeled 3WJ-FA-A647 was incubated with 1×10$^5$ MGC803 and GES-1 cells at 37° C. for 1 h, after washing with PBS for three times, the cells were collected and resuspended in PBS buffer, followed by analyzed with a FACS Calibur (BD Biosciences).

In order to investigate the specificity of RNA nanoparticles binding to MGC803 cells, MGC 803 cells were cultured in a humidified 5% CO2 balanced air incubator at 37° C. for 2 days. All the cells were collected and implanted onto 18 mm glass coverslips in a 12-well tissue culture plate, and culturing was continued for 3 days. After the cells were rinsed 3 times, 500 µL of medium containing prepared RNA nanoparticles was added into each dish and incubated for 30 min. Three dishes of all dishes were first incubated with free folic acids for 30 min, then incubated with RNA nanoparticles, then washed with PBS buffer, and then examined under the dark field microscopy. Dark-field images were obtained on an upright Olympus IX71 optical mi8croscope integrated with a CRi Nuance multispectral imaging system (Cambridge Research & Instrumentation, Inc., Woburn, Mass., USA).

Effects of RNA Nanoparticles on the Silencing of BRCAA1 Gene in MGC803 Cells

MGC803 cells were transfected with a positive BRCAA1 siRNA control using Lipofectamine 2000 (Invitrogen) as the carrier. Two 3WJ-RNA constructs were assayed for the subsequent BRCAA1 gene silencing effects: one harboring folate and BRCAA1 siRNA; and, the other harboring folate and BRCAA1 siRNA scramble control. After 48 h of treatment, total RNAs from MGC803 cells were isolated by using Trizol (Invitrogen) and Direct-zol™ RNA MiniPrep (Zymo Research) according to manufacturer's instructions. First-strand cDNA was obtained by using 1 µg of total RNA and random primers and M-MLV reverse transcriptase (Promega). All reactions were carried out in a final volume of 25 µl and assayed in triplicate. qRT-PCR was performed using a BioRad iQ5 iCycler Detection System with a three-step PCR protocol (95° C. for 10 min, followed by 40 cycles of 95° C. for 5 s, 60° C. for 30 s and 72° C. for 30 s) with Hieff™ qPCR SYBR® Green Master Mix (Yeasen). The data was analyzed by the ΔΔCT method. The primers for BRCAA1 and GAPDH are as follows:

```
BRCAA1:
forward:
                                    (SEQ ID NO: 17)
5'-ACCAAATCTCCCGCAAGG-3';

reverse:
                                    (SEQ ID NO: 18)
5'-CATATTTTCCAGGTCCGACA-3'.

GAPDH:
forward:
                                    (SEQ ID NO: 19)
5'-GAAGGTGAAGGTCGGAGTC-3';

reverse:
                                    (SEQ ID NO: 20)
5'-GAAGATGGTGATGGGATTTC--3'.
```

The qRT-PCR data were treated by using comparative Ct method, the calculation formation is as follows: 2−ΔΔCt; ΔΔCt=(treated group Ct-treated group GAPDH Ct)-(control group Ct-control group GAPDH Ct). The results obtained indicate the relative ratio is calculated that target gene mRNA expression levels in the treated group are divided by mRNA expression level in the control group.

For western blot assays, the total cell lysates were prepared in high KCl lysis buffer (10 mM Tris-HCl, pH 8.0, 140 mM NaCl, 300 mM KCl, 1 mM EDTA, 0.5% Triton X-100 and 0.5% sodium deoxycholate) with complete protease inhibitor cocktail (Roche). Thirty micrograms of protein were separated by SDS-PAGE and electrophoretically transferred to PVDF membranes (Millopore). The membranes were incubated respectively with BRCAA1 antibody (1:2000 diluted), Bcl-2 antibody (1:2000 diluted), Rb antibody (1:2000 diluted), Bax (1:2000 diluted) and β-actin antibody (Epitomics) (1:4000 diluted) for overnight, followed by 1:10000 anti-mouse secondary antibody conjugated with HRP (Epitomics) for 2 h. Membranes were blotted by Westar EtaC ECL kits (Cyanagen Srl) and exposed to film for autoradiography.

Effects of RNA Nanoparticles on Growth and Apoptosis of MGC803 Cells

Effects of prepared RNA nanoprobes on viability of MGC803 cells and GES-1 cells were analyzed using Cell Counting Kit-8 (CCK8) assay (23). MGC803 cells and GES-1 cells were cultured in the 96-well microplate at the concentration of 5000 cells per well and incubated in a humidified 5% CO2 balanced air incubator at 37° C. for 24 h. Except for control wells, the remaining wells were added into medium with prepared RNA nanoparticles, final concentrations were, respectively, 10, 20, 40 and 80 µg/ml, then those cells were continued to culture for 24 h, 48 h and 72 h, respectively, then, the ODs were measured using the thermomultiskan MK3 ELISA plate reader according to the protocol of CCK8 assay kit, and calculated the survival rate of cells. The survival rate of cells can be calculated by the following equation:

Cell viability (%)=optical density(OD) of the treated cells/OD of the non-treated cells×100

The prepared RNA nanoparticles were incubated with MGC803 cells for 48 h, cell apoptosis and necrosis were determined by Annexin V-FITC/PI double staining and quantified by flow cytometry. Briefly, $1 \times 10^5$ MGC 803 cells were harvested 48 h after transfection and resuspended in 100 μL binding buffer containing 5 μl annexin V-FITC and 5 μl PI provided with the Annexin V-FITC/PI Apoptosis Detection Kit (Yeasen) for 15 min at room temperature in the dark. Samples were then analyzed with a FACSCalibur (BD Biosciences). The live cells were identified as Annexin V-FITC$^-$/PI$^-$ (lower left quadrant), early apoptotic cells as Annexin V-FITC$^+$/PI$^-$ (upper left quadrant), late-stage apoptotic cells as Annexin V-FITC$^+$/PI$^-$ (upper right quadrant), and necrotic cells as Annexin V-FITC$^-$/PI$^+$ (upper left quadrant). Annexin V-FITC/PI Apoptosis Detection Kit was purchased from Yeasen Corporation (Shanghai, China).

RNA Nanoparticles for NIR Fluorescent Imaging of In Vivo Gastric Cancer

Female athymic nude mice (18-22 g) were purchased from Shanghai Slac Laboratoty Animal Co. Ltd (Shanghai, China). For the establishment of tumor model, MGC803 cells were resuspended in PBS and $2 \times 10^6$ cells/site was subcutaneously injected in the right flank. When the tumor nodules had reached a volume of 0.1-0.3 cm$^3$ after approximately 3 weeks post-injection, mice were used for biodistribution and imaging studies. For tumor imaging, FA-Alexa Fluor 647-labeled pRNA-3WJ nanoparticle (about 20 nmol in PBS buffer, equal 32 mg/kg) was administrated intravenously into the MGC-803-tumour-bearing mice. Time-course fluorescent images (excitation: 630/20 nm, emission: 700/30 nm, integration time: 15 s) were acquired on a Bruker In-Vivo F PRO imaging system (Billerica, Mass.). All the post injection images were captured at the same parameter setting and are scaled to the same maximum values. For the ex vivo imaging, the mice (3 mice per time point) were then sacrificed and collected tumors and the major organs after 3, 24,48, 96 h and 7 day intravenously (iv) injection. Excised tumor and organs were imaged by the Bruker In-Vivo F PRO imaging system with the same parameters as mentioned above.

RNA Nanoparticles for Targeted Therapy of In Vivo Gastric Cancer

Nude mice loaded with gastric cancer MGC803 cells were prepared according to the previous reports (12-15), and were randomly divided into three groups: test group (10 mice) (FA-pRNA-3WJ-BRCAA1siRNA, 1 mg/kg body weight); control group (10 mice) (FA-pRNA-3WJ-Scram siRNA, 1 mg/kg body weight) and blank control (10 mice) (untreated). When the tumor sizes reached about 5 mm in diameter, the nude mice were injected with prepared RNA nanoparticles in PBS via tail vein (1 mg/kg body weight). Every two days, the tumor volume was measured, up to 15 days. Then, these mice were sacrificed.

Effects of RNA Nanoparticles on Important Organs

The mice in testing group were sacrificed after being raised for 15 days. For histological evaluation, excised important organs including heart, liver, spleen, lung and kidney were frozen and embedded by medium at –20° C., and then were sectioned into 8 μm slices, then were stained by hematoxylin and eosin (HE) stain method, and were observed by microscopy to confirm whether there is pathological lesion in important organs existed.

Statistical Analysis

Each experiment was repeated three times in duplicate. The results were presented as mean±SD. Statistical differences were evaluated using the t-test and considered significance at P<0.05.

Results

Construction and Characterization of Triple-Functional pRNA-3WJ Nanoparticles

Figure 12A:
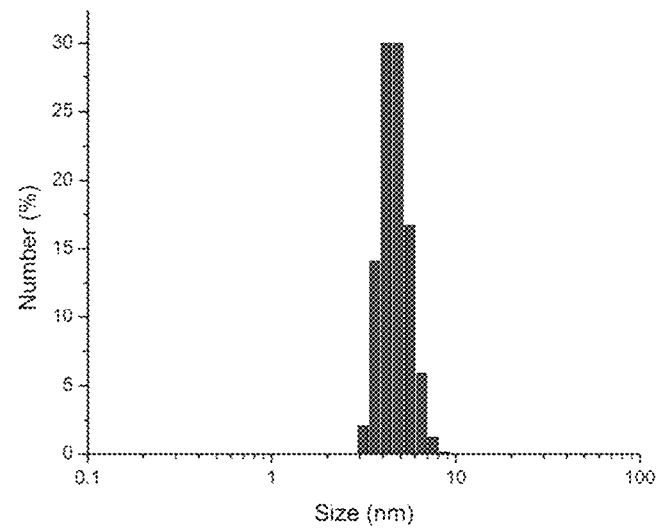
FIG. 12A is an graph showing the size of 3WJ-BRCAA1 siRNA nanoparticle.
Figure 12B:
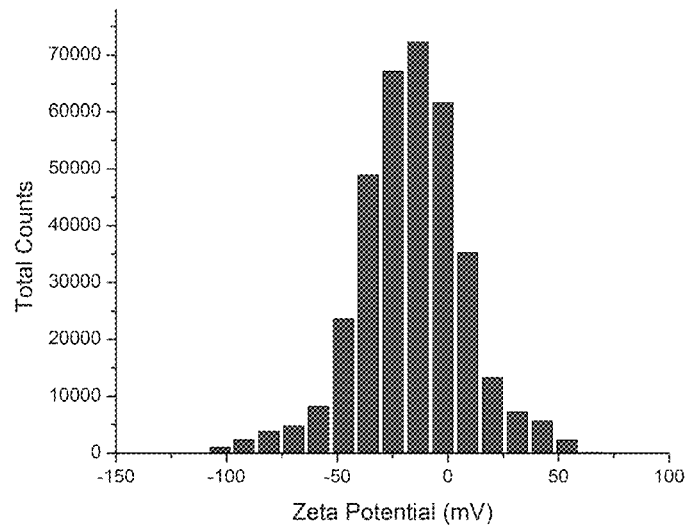
FIG. 12B is a graph showing the zeta potential of 3WJ-BRCAA1 siRNA nanoparticle. The RNA nanoparticles were dissolved in 1×TMS buffer with concentration at 1.5 μM and then were measured by Zetasizer nano-ZS (Malvern Instrument). The data showed that the size of the nanoparticle is 5.20±0.83 nm in diameter, and the zeta potential is −16.57±0.75 my, as shown in Figure S1A and S1B. The data were obtained from three independent measurements.

The pRNA-3WJ nanoparticles were prepared by mixing the three strands $a_{3WJ}$, $b_{3WJ}$, and $c_{3WJ}$ respectively, at equal molar ratio (FIG. 1a). Atomic force microscopy (AFM) image highly suggested the formation of homogeneous triangular branched architectures, confirming that pRNA-3WJ nanoparticles were successfully prepared (FIG. 1b). Regarding the RNA nanoparticles' size and surface charge, the dynamic light scattering experiments showed that the size of the nanoparticle is 5.20±0.83 nm in diameter, and the zeta potential is –16.57±0.75 my, as shown in FIGS. 12A and 12B.

Figure 13:
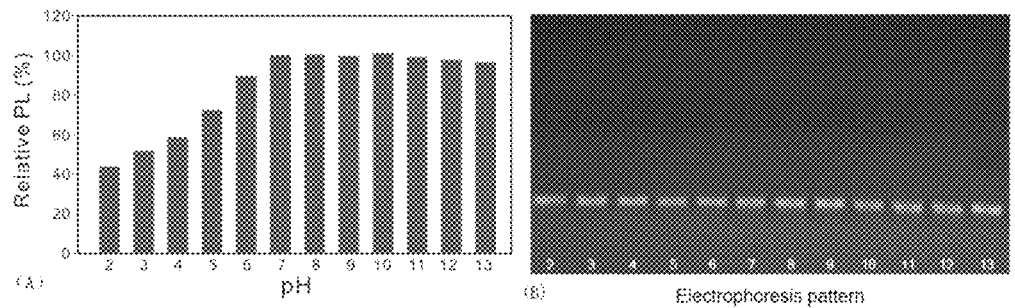
FIG. 13 includes a graph and an image showing the effects of pH on the fluorescent intensity and stability of RNA nanoparticles.

In order to evaluate the effects of a wide pH range on the stability of RNA nanoparticles, the prepared RNA nanoparticles were dispersed in varied pH buffers (RNA nanoparticles/buffer=1:1(v/v)) for 12 h. The details of the preparation of a series of buffer solutions with pH 2 to 13 were shown in Table 1. The effects of pH on the fluorescent intensity of RNA nanoparticles is investigated. As shown in FIG. 13A, in the range of pH 2 to 13, RNA nanoparticles exhibited different fluorescent intensity, and in the range of pH 5-9, RNA nanoparticles displayed more than 90% strong fluorescent signals. The study used 1.2% agarose gel electrophoresis to characterize the stability of prepared RNA nanoparticles. As shown in FIG. 13B, tested RNA nanoparticles displayed identical position and similar brightness on the gel, no degradation, suggesting that the RNA nanoparticles are stable in the range of pH 2 to 13.

Figure 14:
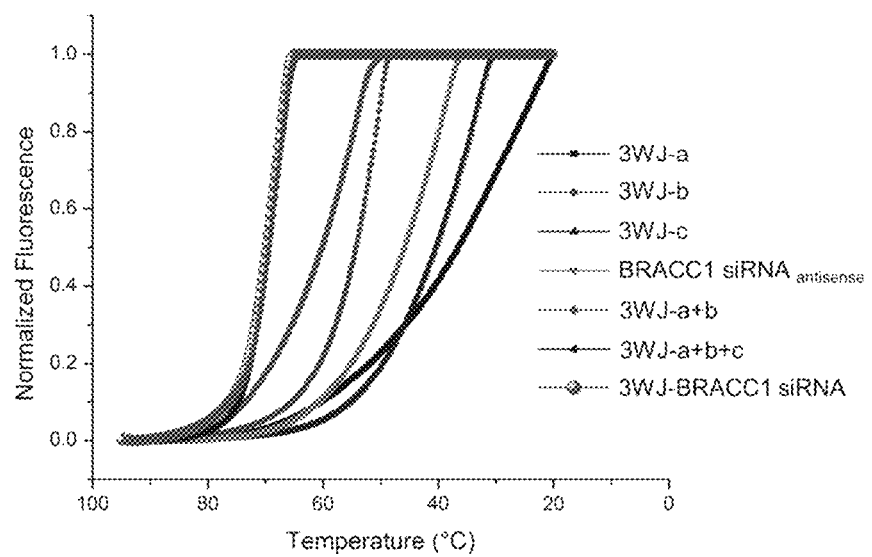
FIG. 14 is a graphs showing the determination of the melting temperature of the 3WJ-BRCAA1 siRNA nanoparticle.

The melting temperature of the 3WJ-BRCAA1 siRNA nanoparticle was determined as 69.2±0.9° C. by real-time PCR, as shown in FIG. 14. Melting experiments were conducted by monitoring the fluorescence of the RNA nanoparticles or the assembly intermediates using the Light-Cycler 480 Real-Time PCR System (Roche). 1×SYBR Green dye was used for all the experiments. The RNA samples were dissolved in 1×TMS buffer and slowly cooled from 95 to 20° C. The melting temperature of the 3WJ-BRCAA1 siRNA nanoparticle was determined as 69.2±0.9° C. The data represents the mean and standard deviation of three independent experiments.

Figure 15:
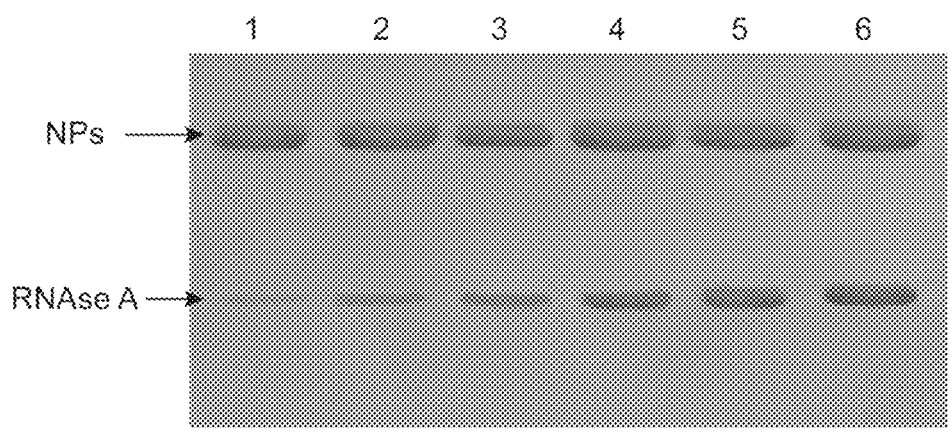
FIG. 15 is an image showing the effects of RNAase A on the stability of RNA nanoparticles. Lane 1: 10 U RNAase A; Lane2: 50 U RNAase A, Lane 3: 100 U RNAase A, Lane 4: 500 U RNAase A; Lane 5: 1000 U RNAase A; Lane 6: 10000 U RNAase A. RNA nanoparticles on different lanes exhibited identical position, similar brightness and no obvious degradation, suggesting that prepared RNA nanoparticles have good stability against RNase A (less than 10000 U)-mediated degradation.

Effects of RNAase A on the stability of RNA nanoparticles were also investigated. RNase A-free purified water was used to dilute RNAse A (Sigma Company). The resulting solutions were respectively exhibited different concentration of RNAse A (10 U, 50 U, 100 U, 500 U, 1000 U, 10000 U). Then each tube was respectively added 1□g RNA nanoparticles, incubated at 37° C. for 12 h, and finally 10% SDS-PAGE gel electrophoresis was used to examine the effects of RNAse A on the stability of RNA nanoparticles. As shown in FIG. 15, RNA nanoparticles on different lanes exhibited identical position, similar brightness, no obvious degradation, which highly suggests that prepared RNA nanoparticles own good stability against RNase A (less than 10000 U) degradation.

The resultant pRNA-3WJ nanoparticles are thermodynamically and chemically stable, which makes them an attractive candidate for in vivo nano-delivery for the purpose of cancer detection or treatment. In this study, folate is incorporated, as targeting ligand; Alexa$_{647}$, as imaging module; and BRCAA1 siRNA (or scrambled control) into the pRNA-3WJ scaffold.

Binding Efficiency of pRNA Nanoparticles to Gastric Cancer Cell

Figure 2:
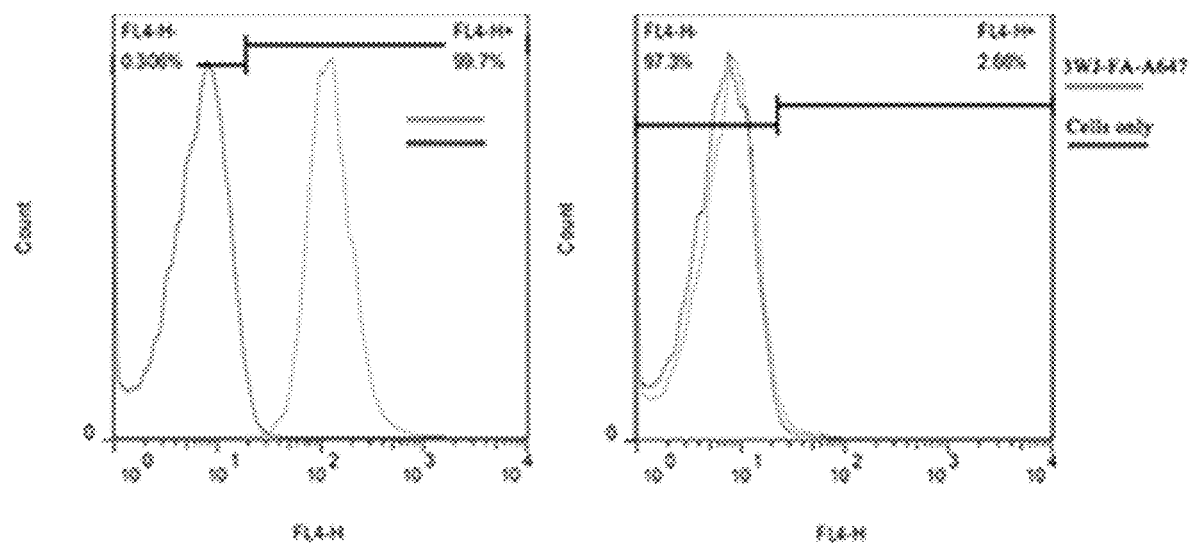
FIG. 2 includes graphs showing flow cytometry analysis for specific binding of 3WJ-FA-A647 nanoparticles to MGC803 cells (left, folate positive), GES-1 cells (right, folate negative control).

Flow cytometry data in FIG. 2 showed that the prepared 3WJ-FA-A647 nanoparticles can bind with the MGC803 cells with almost 100% binding efficiency, while the GES-1 cells display a weak signal, which highly suggested that the prepared RNA nanoparticles did not bind with GES-1 cells. Results also demonstrate that folic acid receptor exhibits over-expression on the surface of MGC803 cells, no expression on the surface of GES-1 cells, similar to a previous report (15).

Effects of RNA Nanoparticles on the Silence of BRCAA1 gene in MGC803 Cells

Figure 3:
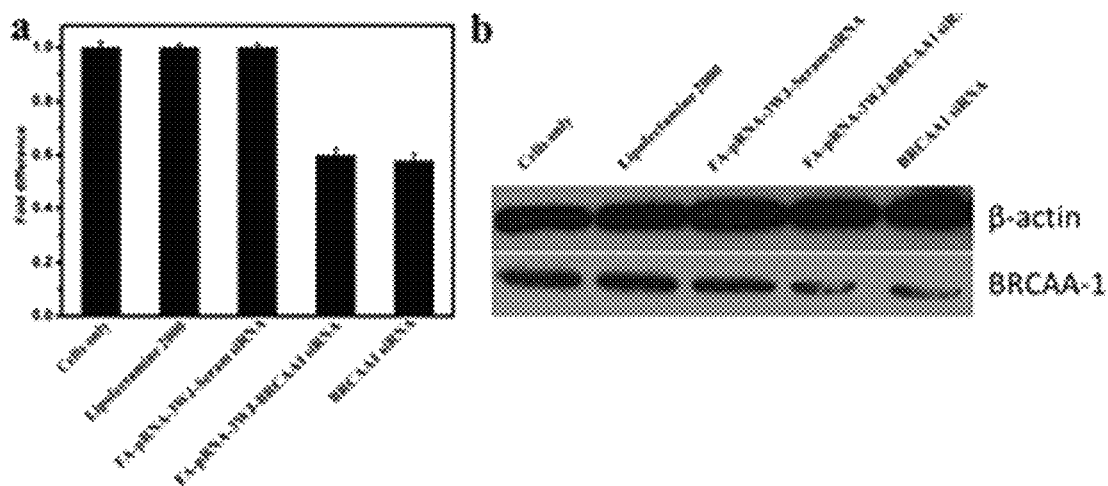
FIG. 3 shows the BRCAA1 silencing effects of FA-pRNA-3WJ-BRCAA1siRNA assayed by (a) qRT-PCR (GADPH is the endogenous control) (there existed statistical difference between FA-pRNA-3WJ-BRCAA1siRNA group and FA-pRNA-3WJ-Scramb-siRNA group, $P<0.01$) and (b) western blot assay ($\beta$-actin bands served as loading control).

The qRT-PCR results in FIG. 3a showed that, prepared FA-pRNA-3WJ-BRCAA1 siRNA nanoparticles could silence expression of BRCAA1 gene in MGC803 cells after incubating with MGC803 cells for 48 h, in contrast, prepared FA-pRNA-3WJ-Scram siRNA nanoparticles could not silence expression of BRCAA1 gene in MGC803 cells after incubation for 48 h, between two groups, there existed statistical difference (P<0.01). Compared with BRCAA1 siRNA, prepared FA-pRNA-3WJ-BRCAA1 siRNA nanoparticles achieved similar silencing efficiency of BRCAA1 gene in MGC803 cells. The Ct, Delta Ct, and Delta Delta Ct values for the qRT-PCR assay are shown in Table 2. Additionally, as shown in FIG. 3b, Western blotting results further confirmed that prepared FA-pRNA-3WJ-BRCAA1 siRNA nanoparticles and BRCAA1 siRNA could down-regulate BRCAA1 expression in MGC803 cells, while prepared FA-pRNA-3WJ-Scram siRNA nanoparticles had little down-regulation of BRCAA1 protein expression in MGC803 cells, thus showing prepared FA-pRNA-3WJ-BRCAA1 siRNA nanoparticles can specifically silence expression of BRCAA1 protein in MGC803 cells. Importantly, the silencing potency was comparable to the Lipofectamine 2000 carried BRCAA1 siRNA group.

TABLE S2

The expression levels of BRCAA1 normalized to the exogenous GAPDH mRNA in the treated group and control group (the Ct, Delta Ct, and Delta Delta Ct values).

| group | Ct | ΔCt | ΔΔCt | $2^{-ave\ \Delta\Delta\ Ct}$ | P value |
|---|---|---|---|---|---|
| GAPDH | 6.943 | | | | |
| BRCAA1-siRNA | 14.931 | 7.988 | 1.435 | 0.485 | 0.005 |
| FA-pRNA-3WJ-Scramb-siRNA | 20.566 | 13.623 | 4.427 | 0.051 | 0.001 |
| GAPDH | 6.944 | 1 | | | |
| FA-pRNA-3WJ-BRCAA1-siRNA | 15.194 | 8.252 | 1.507 | 0.404 | 0.000 |
| GAPDH | 6.942 | 1 | | | |

Effects of RNA Nanoparticles on Growth and Apoptosis of Gastric Cancer Cell MGC803

Figure 4:
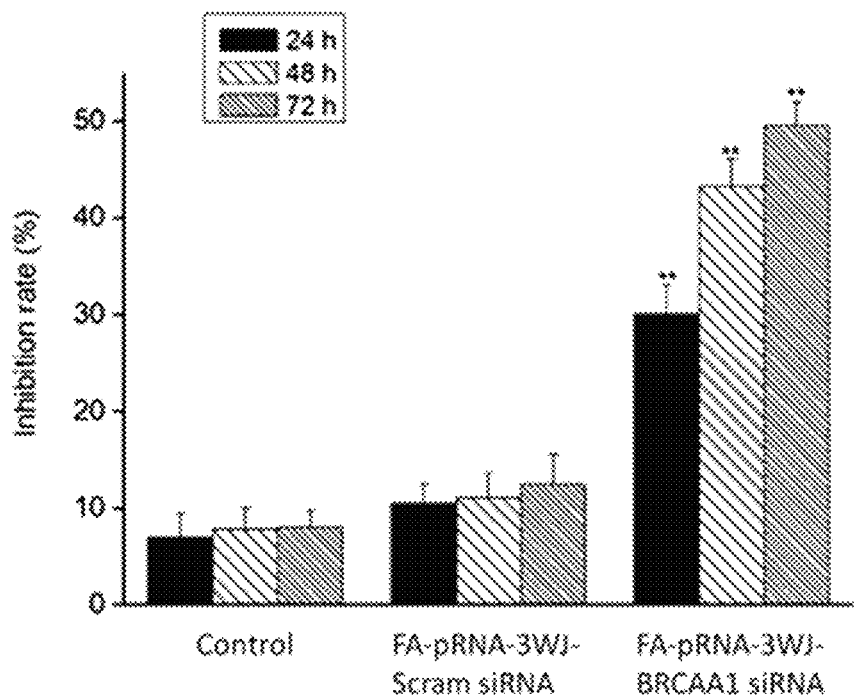
FIG. 4 is a graph showing inhibition of the growth of MGC803 cells by the nanoparticle of FA-pRNA-3WJ-BRCAA1siRNA using CCK8 (Cell Counting Kit-8) assays. The "Control" is non-treated MGC803 cells.

As shown in FIG. 4, MGC 803 cells were treated with 400 μg/mL FA-pRNA-3WJ-BRCAA1 siRNA nanoparticles for 24 h, 48 h and 72 h, the inhibition rate of MGC 803 cells increased as the incubation time increased, at 48 h, maximal inhibition rate of MGC803 cells is 44.5±2.6%, compared with FA-pRNA-3WJ-Scram siRNA group, inhibition rate is 12.5±1.9%, there existed statistical difference between two groups, P<0.01.

Figure 5:
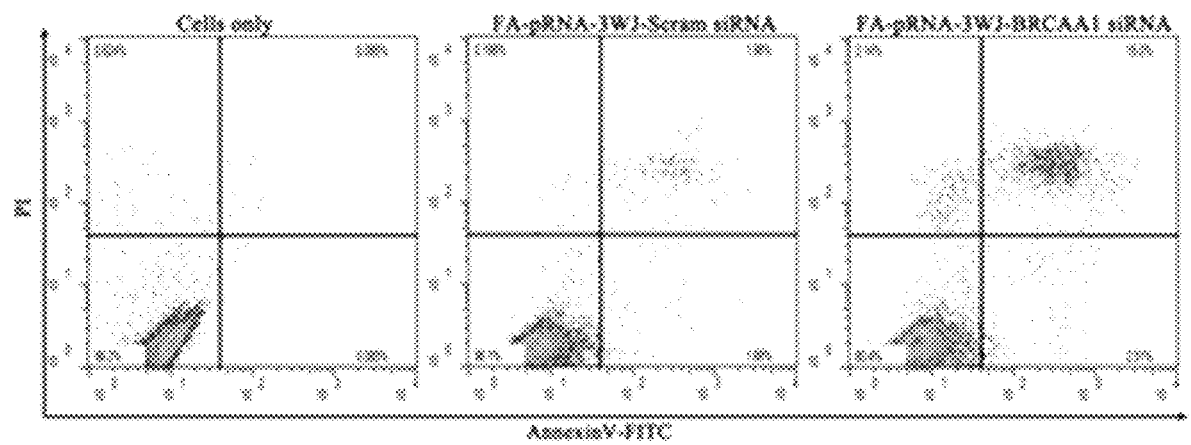
FIG. 5 includes graphs showing determination of cell death by flow cytometry of Annexin V-FITC/PI staining in MGC803 cells transfected with 25 nM FA-pRNA-3WJ-BRCAA1siRNA or FA-pRNA-3WJ-Scram-siRNA for 48 h.
Figure 16:
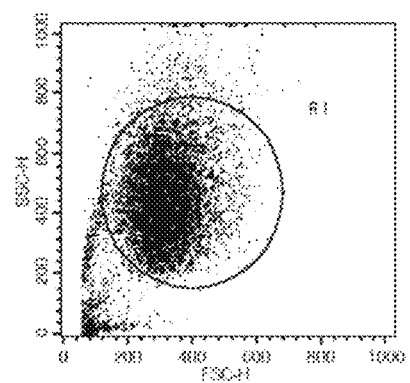
FIG. 16 is a graph showing light scattering plots of MGC803 cells at 48 h treated with FA-pRNA-3WJ-BRCAA1-siRNA nanoparticles.

Previous study shows that BRCAA1 can inhibit MGC803 cell apoptosis and improve the proliferation of MGC803 cells, it is hypothesized that the performed RNA interference (RNAi) by RNA nanoparticles could induce MGC803 cell apoptosis. As shown in FIG. 5, the transfection with 25 nM FA-pRNA-3WJ-BRCAA1 siRNA in MGC803 cells induced 2.51% of early apoptotic cells and 15.0% of late apoptotic cells, respectively, in the normal control, MGC803 cells exhibited 0.085% of early apoptotic cells, there existed statistical difference between treated group with FA-pRNA-3WJ-BRCAA1 siRNA and control group, P<0.05. The light scattering plot of MGC 803 cells treated with FA-pRNA-3WJ-BRCAA1 siRNA nanoparticles for 48 h is shown in FIG. 16. These results show that prepared FA-pRNA-3WJ-BRCAA1 siRNA nanoparticles can induce apoptosis of MGC803 cells.

Fluorescent RNA Nanoparticles for In Vivo Imaging of Gastric Cancer

Figure 6:
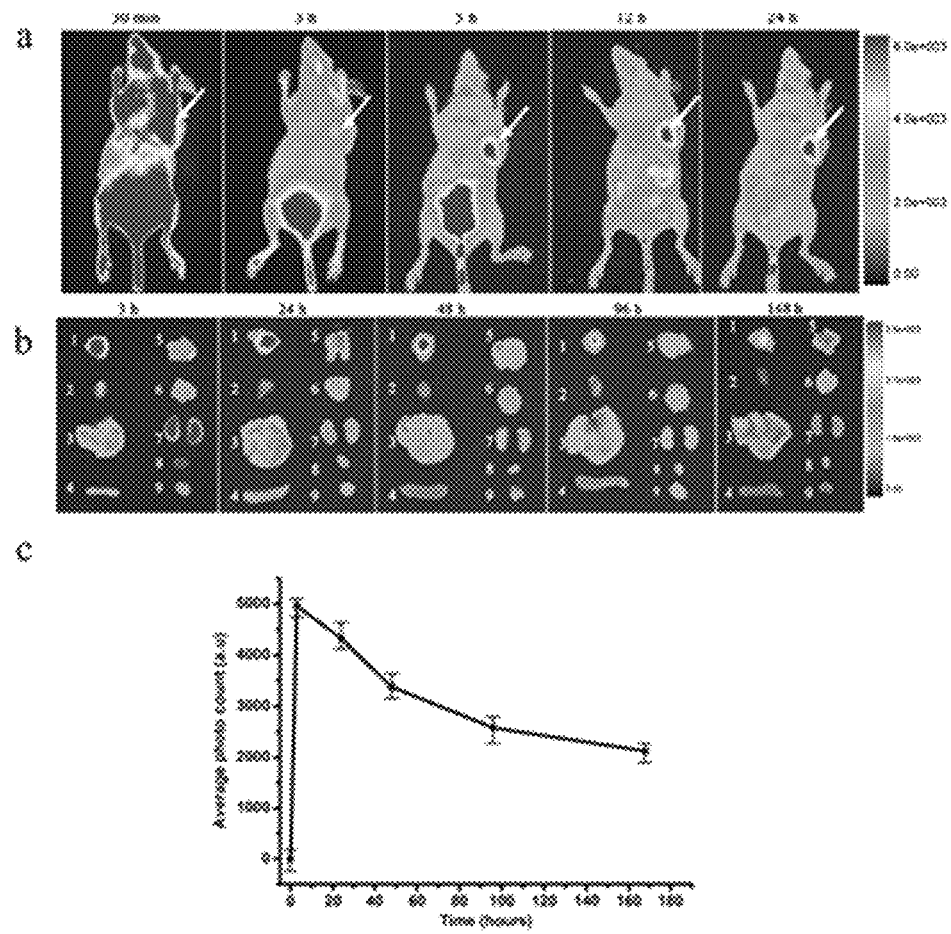
FIG. 6A includes images showing representative in vivo fluorescence images of MGC803-tumour-bearing mouse after iv-injected with FA-AlexaFluor647-labeled pRNA nanoparticle. The tumor areas are indicated with arrows.
FIG. 6B shows representative ex vivo images of tumors and organs. Labels: 1, tumor; 2, heart; 3, liver; 4, spleen; 5, lung; 6, Stomach; 7, kidneys; 8, bladder; 9, muscle.
FIG. 6C is a graphs showing the average fluorescence intensities from the tumor areas of post-injection (3 mice per time point). The error bars represent SEM (n=3).

It has been reported that unmodified siRNA ribonucleic acid sequences have extremely poor pharmacokinetic properties due to short in vivo half-life and fast kidney clearance caused by their small size (hydrodynamic diameters, HDs; typically <5 nm, which is smaller than the kidney filtration threshold (KFT) of 5.5 nm). Tumor targeting efficiency by RNA nanoparticles was investigated by collecting and analyzing in situ fluorescence images of MGC803 xenografts in nude mice at different post-injection (p.i.) time points (FIGS. 6a and c). Tumor area was hardly distinguished in the mouse in the first 30 min p.i. because of the strong fluorescence background in normal tissues. However, as the time increased, the decrease in the fluorescence background of normal tissues and the accumulations at the tumor site caused the tumor area became readily defined 5 h p.i. Ex vivo images of normal tissues, organs, and tumors taken from the RNA nanoparticles-injected mice showed that the tumors taken at 5 and 24 h p.i. exhibited the strongest signal (FIG. 6b). In terms of tumor accumulation kinetics, RNA nanoparticles reached their highest accumulation within 5 h and remained in the tumor site 96 h p.i., which indicted the high tumor targeting efficiency and tumor retention capability of the constructed RNA nanoparticles.

RNA Nanoparticles for In Vivo Targeted Therapy of siRNA to Gastric Cancer

Figure 7:
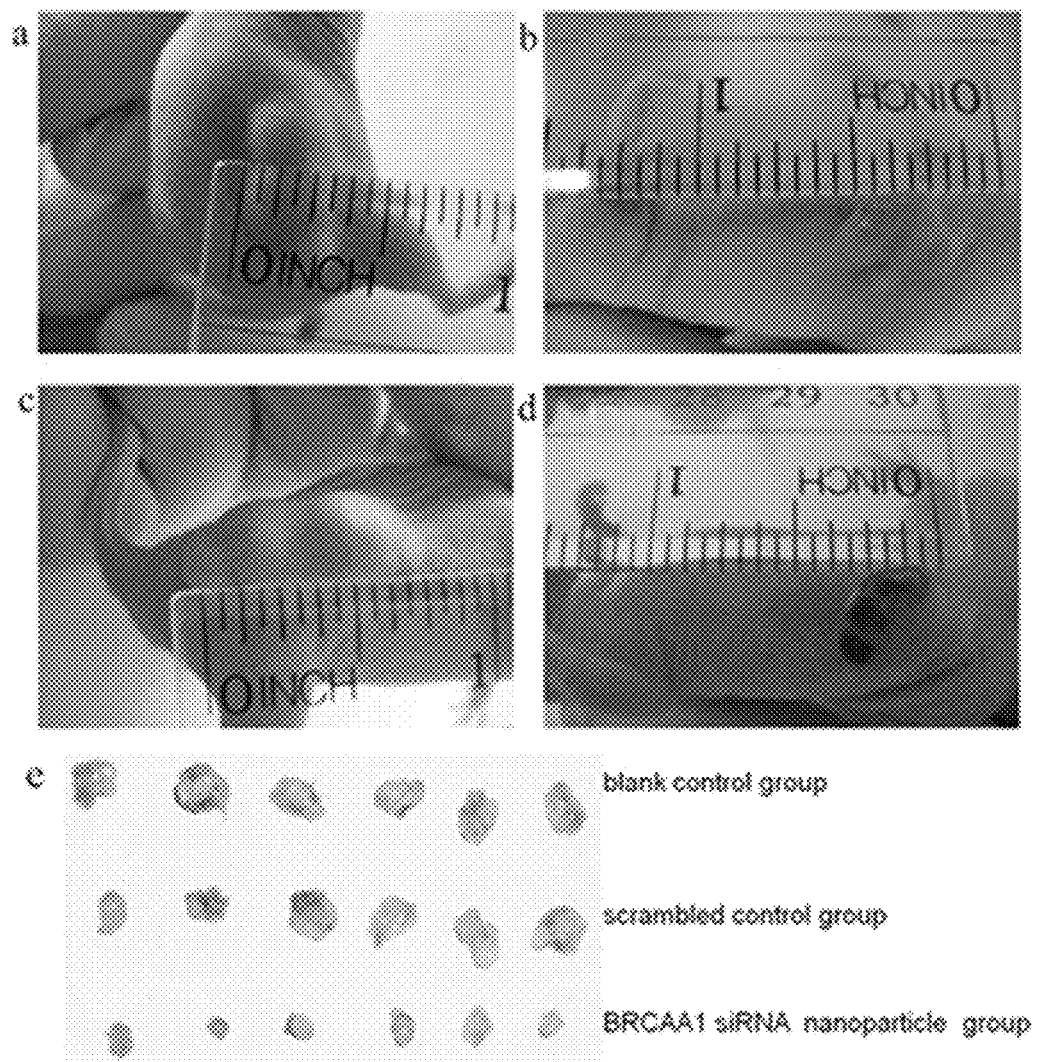
FIG. 7 includes images showing tumor sizes in test group and control group under different days
Figure 8:
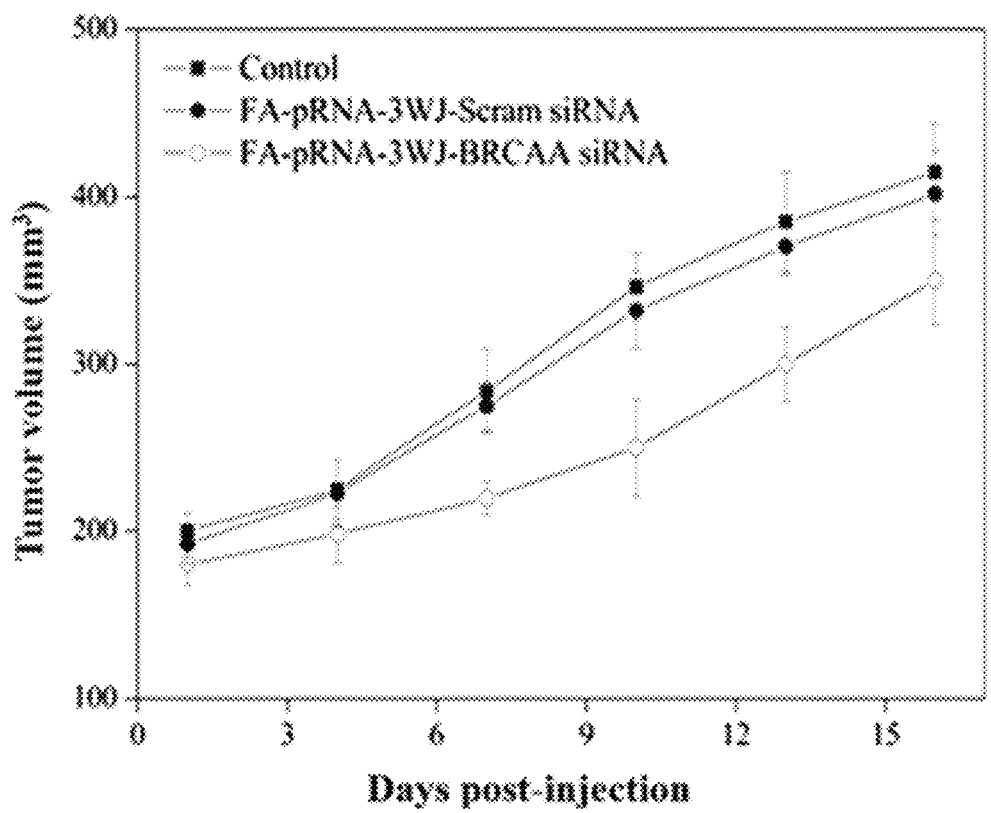
FIG. 8 is a graph showing the tumor size curve as the post-treatment time increases. There existed statistical difference between FA-pRNA-3WJ-BRCAA1siRNA treated group and FA-pRNA-3WJ-Scram-siRNA treated group, P<0.01.

As shown in FIGS. 7 and 8, the tumor in the mouse without treatment grew very rapidly, the size of tumor enlarged as a control. In contrast, the tumor in mice with treatment showed regressed growth and the size of tumor is smaller comparing to controls. The difference between FA-pRNA-3WJ-BRCAA1siRNA treated group and FA-pRNA-3WJ-Scram-siRNA treated group was statistically different (P<0.01). The result fully demonstrated that prepared FA-pRNA-3WJ-BRCAA1 siRNA nanoparticles can specifically inhibit the growth of gastric cancer cells in vivo.

Undetectable of Organ Damage by RNA Nanoparticles after Systemic Injection.

Figure 9:
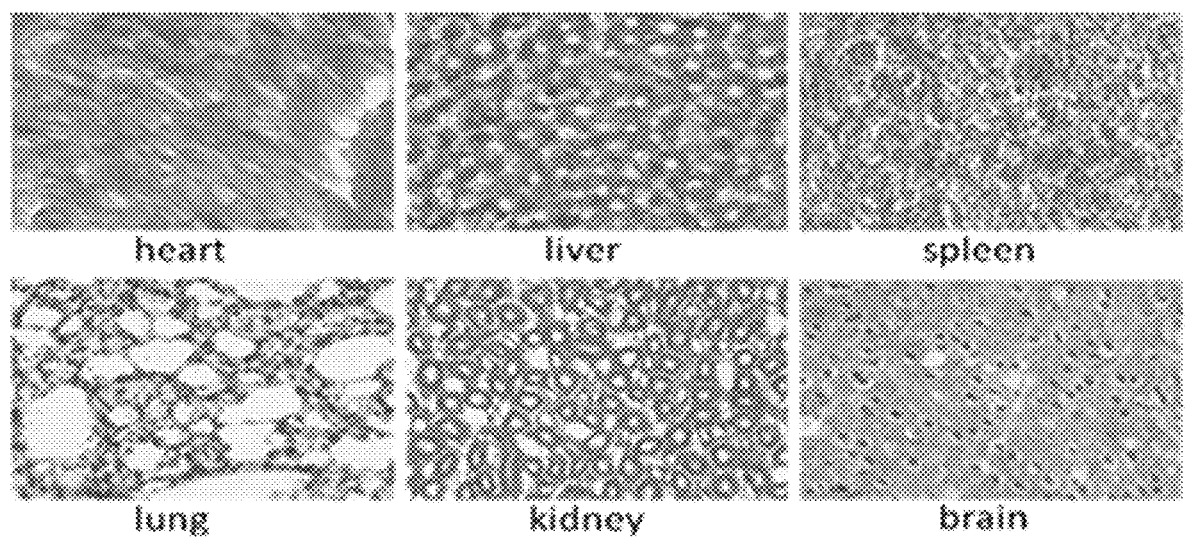
FIG. 9 includes images showing the result of HE immunostaining of important organs showing the undetectable damage.

Harris Hematoxylin and Eosin (HE) staining are used to check the potential damage to important organs including the heart, liver, spleen, lung and kidney by the RNA nanoparticles. As shown in FIG. 9, no obvious tissue damages were observed, which indirectly suggested that the prepared RNA nanoparticles displayed good biocompatibility and no negative effects on important organs in the body was observed.

In this study, in order to investigate the feasibility of applying RNA nanoparticles as theranostic agents for gastric cancer diagnosis and therapy, the pRNA-3WJ nanoparticle is designed consisting of three fragments, $a_{3WJ}$, $b_{3WJ}$ and $c_{3WJ}$, and functionalized with folate, as targeting ligand; $Alexa_{647}$, as imaging module; and BRCAA1 siRNA (or scrambled control), as therapeutic module, respectively. FA-pRNA-3WJ-BRCAA1 siRNA nanoparticles is prepared and the resulting RNA nanoparticles showed good pH and thermodynamic stability, good stability against RNase A (less than 10000 U) degradation, and exhibited stability of fluorescent intensity. These results demonstrated that the prepared RNA nanoparticles should be very stable in the blood circulation and can act as high efficient theranostic agent for targeted imaging and siRNA therapy of gastric cancer in vivo, which lay foundation for RNA nanoparticles' further clinical application.

Nanotoxicity of nanotheranostic agents has caused broad attention. In this study, prepared RNA nanoparticles did not exhibit obvious toxicity. After being injected into in vivo blood circulation via tail vain, RNA nanoparticles gradually accumulated in the site of in vivo tumor within 6 h p.i., clearly displayed the imaging of tumor tissues, and exhibited specific targeting ability. The RNA nanoparticles were also proved to be able to retention in the tumor for long time and generate tumor regression effects.

In addition, the alteration of biochemical parameters in the mice after treating with FA-pRNA-3WJ-BRCAA1 siRNA nanoparticles was investigated as shown in Table 3 and o obvious tissue damages were observed for liver and kidneys. To study the effects of RNA nanoparticles on blood biochemical parameters, blood samples were centrifuged twice at 3000 rpm for 10 min. Liver function was evaluated with serum levels of alanine aminotransferase (ALT), aspartate aminotransferase (AST). Nephrotoxicity was determined by blood urea nitrogen (BUN) and creatinine (Cr). These parameters were all assayed using a Hitachi 7600 Automatic Biochemical Autoanalyzer.

TABLE S3

Blood biochemical examination results

|  | WBC | AST | ALT | Cr | UN |
|---|---|---|---|---|---|
| FA-pRNA-3WJ-BRCAA1-siRNA NPs |  |  |  |  |  |
| 20 µg |  |  |  |  |  |
| 1 day | $4.3 \times 10^5$ | 32 | 35 | 0.005 | 0.041 |
| 7 day | $4.2 \times 10^5$ | 33 | 35 | 0.005 | 0.042 |
| 14 day | $4.4 \times 10^5$ | 33 | 35 | 0.006 | 0.043 |
| 60 µg |  |  |  |  |  |
| 1 day | $5.2 \times 10^5$ | 35 | 42 | 0.007 | 0.038 |
| 7 day | $4.9 \times 10^5$ | 33 | 42 | 0.004 | 0.039 |
| 14 day | $4.5 \times 10^5$ | 34 | 42 | 0.005 | 0.039 |
| FA-pRNA-3WJ-Scramb-siRNA |  |  |  |  |  |
| 20 µg |  |  |  |  |  |
| 1 day | $4.2 \times 10^5$ | 32 | 36 | 0.004 | 0.052 |
| 7 day | $4.2 \times 10^5$ | 34 | 37 | 0.002 | 0.054 |
| 14 day | $4.2 \times 10^5$ | 35 | 38 |  |  |
| 60 µg |  |  |  |  |  |
| 1 day | $4.2 \times 10^5$ | 32 | 34 | 0.031 | 0.045 |
| 7 day | $4.2 \times 10^5$ | 33 | 35 | 0.036 | 0.037 |
| 14 day | $4.2 \times 10^5$ | 35 | 37 | 0.034 | 0.038 |
| Control |  |  |  |  |  |
| 0 | $3.9 \times 10^5$ | 28 | 32 | 0.001 | 0.008 |

Further HE staining results also confirmed that prepared RNA nanoparticles did not damage important organs such as brain, heart, lungs, liver and kidneys. Therefore, it can be confirmed that the prepared RNA nanoparticles should be safe for in vivo application.

Figure 10:
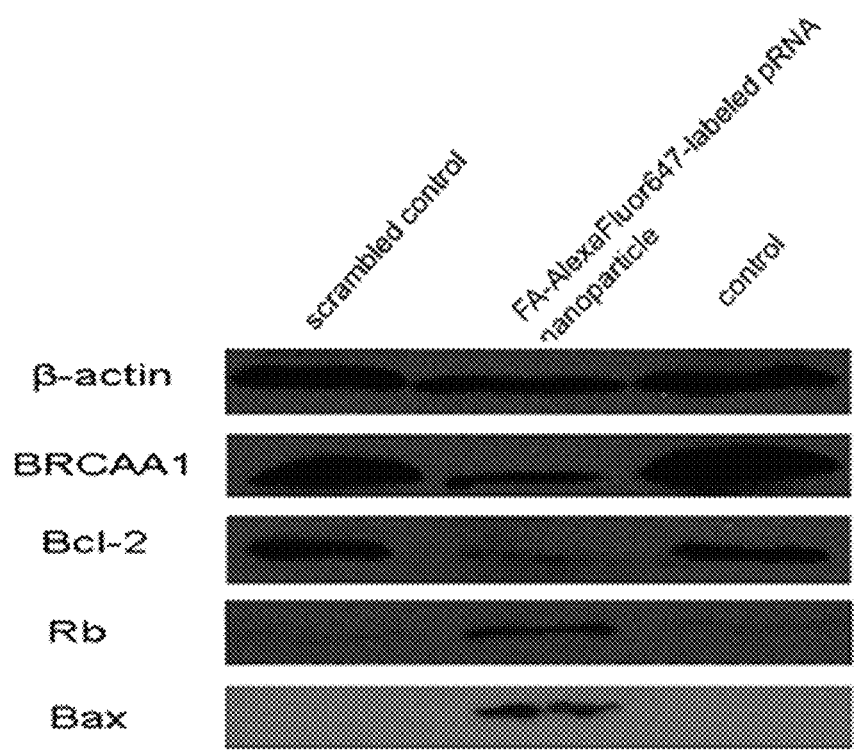
FIG. 10 is an images showing the expression of related apoptosis proteins of MGC803 cells at 48 h post-treatment by Western blotting. 1: scrambled control; 2: FA-AlexaFluor647-labeled pRNA nanoparticle; 3: control.
Figure 11:
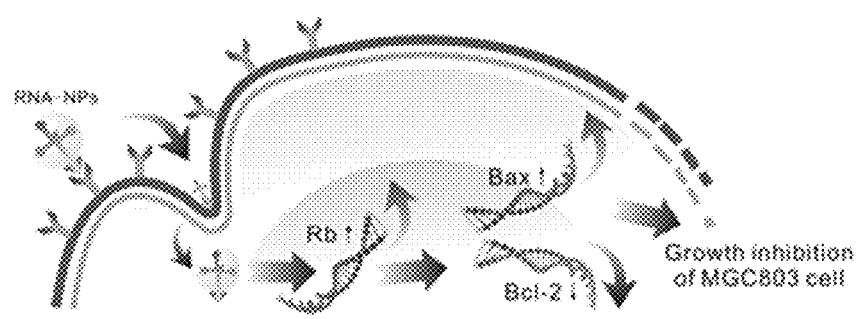
FIG. 11 is a diagram showing the potential mechanism of RNA nanoparticles for gastric cancer therapy.

In this study, the results of in vivo evaluation of therapeutic efficacy also showed that the prepared RNA nanoparticles can actively target in vivo gastric cancer tissues and inhibited tumor growth significantly. However, the concrete molecular mechanism is not well understood. In order to investigate the potential molecular mechanism, Western blotting is used to detect the expression level of BRCAA1, Bcl-2, Rb and Bax in MGC803 cells treated with prepared RNA nanoparticles for 24 h and 48 h. As shown in FIG. 10, RNA nanoparticles can down-regulate or silence the expression of BRCAA1 gene, down-regulate expression of Bcl-2 gene, adversely up-regulate expression of Rb and Bax genes in MGC803 cells. Based on these results, a molecular mechanism of RNA nanoparticle induced MGC803 growth inhibition is studied: the prepared RNA nanoparticles (FA-pRNA-3WJ-BRCAA1 siRNA) actively bind to the folic acid receptor on the surface of MGC803 cells via folic acids conjugated on the RNA nanoparticles, and then induce the endocytosis of RNA nanoparticles into tumor cytoplasm. The double-stranded BRCAA1 siRNA region on the RNA nanoparticle can be recognized by RNA-induced silencing complex (RISC) in the cytoplasm and processed. The released siRNA antisense strand can further recognize target BRCAA1 mRNA, degrade it, and result in silence of BRCAA1 gene in MGC803 cells. The down regulate or silencing of the BRCAA1 gene will cause subsequent down-regulation of Bcl-2 gene, and further up-regulation of Rb and Bax gene, which will end up with inducing cell apoptosis and inhibiting the cell growth. The proposed mechanism is summarized in FIG. 11 and the concrete study of the regulation signal pathway is under way.

In recent years, BRCAA1 gene, as an important member of ARID family, called as ARID4B, has been found to involve in the regulation of the male fertility and stem cells, ARID4B protein can regulate Rb binding protein 1, which highly suggest that ARID4B may be a tumor suppressor.

Throughout this document, various references are mentioned. All such references are incorporated herein by reference, including the references set forth in the following list.

REFERENCES

1. Ferlay, J. et al. Estimates of worldwide burden of cancer in 2008: GLOBOCAN 2008. *Int. J. Cancer.* 127, 2893-2917 (2010).
2. Jemal, A. et al. Global cancer statistics. *CA Cancer J. Clin.* 61, 69-90 (2011).
3. Takahashi, T., Saikawa, Y. & Kitagawa, Y. Gastric cancer: current status of diagnosis and treatment. *Cancers* (Basel). 5, 48-63 (2013).
4. Dicken, B. J. et al. Gastric adenocarcinoma: review and considerations for future directions. *Annals of surgery.* 241, 27-39 (2005).
5. Uemura, N. et al. *Helicobacter pylori* infection and the development of gastric cancer. *New England Journal of Medicine.* 345, 784-789 (2001).
6. Comis, R. L. & Carter, S. K. A review of chemotherapy in gastric cancer. *Cancer.* 34, 1576-1586 (1974).
7. Kuo, C. Y., Chao, Y. & Li, C. P. Update on treatment of gastric cancer. *Journal of the Chinese Medical Association: JCMA.* (2014).
8. Proserpio, I. et al. Multimodal treatment of gastric cancer. *World journal of gastrointestinal surgery.* 6, 55-58 (2014).
9. Zhang, D. & Fan, D. New insights into the mechanisms of gastric cancer multidrug resistance and future perspectives. *Future Oncol.* 6, 527-537 (2010).

10. Cui, D. X. et al. A microarray-based gastric carcinoma prewarning system. *World J Gastroenterol.* 11, 1273-82 (2005).
11. Zhang, Y. X. et al. Identification of volatile biomarkers of gastric cancer cells and ultrasensitive electrochemical detection based on sensing interface of Au—Ag alloy coated MWCNTs. *Theranostics.* 4, 154-62 (2014).
12. Wang, K. et al. BRCAA1 monoclonal antibody conjugated fluorescent magnetic nanoparticles for in vivo targeted magnetofluorescent imaging of gastric cancer. *J Nanobiotechnol.* 1, 9-23 (2011).
13. Ruan, J. et al. HER2 monoclonal antibody conjugated RNase-A-associated CdTe quantum dots for targeted imaging and therapy of gastric cancer. *Biomaterials.* 33, 7093-7102 (2012).
14. He, M. et al. Dual phase-controlled synthesis of uniform lanthanide-doped $NaGdF_4$ upconversion nanocrystals via an OA/ionic liquid two-phase system for in vivo dual-modality imaging. *Advanced Functional Materials* 21, 4470-4477 (2011).
15. Huang, P. et al. Folic acid-conjugated silica-modified gold nanorods for X-ray/CT imaging-guided dual-mode radiation and photothermal therapy. *Biomaterials.* 32, 9796-9809 (2011).
16. Huang, P. et al. Light-triggered theranostics based on photosensitizer-conjugated carbon dots for simultaneous enhanced-fluorescence imaging and photodynamic therapy. *Adv. Mater.* 24, 5104-5110 (2012).
17. Zhou, Z. J. et al. Folic acid-conjugated silica capped gold nanoclusters for targeted fluorescence/X-ray computed tomography imaging. *Journal of Nanobiotechnology.* 11, 17 (2013).
18. Zhang, C. L. et al. Glutathione-capped fluorescent gold nanoclusters for dual-modal fluorescence/X-ray computed tomography imaging. *J. Mater. Chem. B.* 1, 5045-5053 (2013).
19. Yang, W., Raufi, A. & Klempner, S. J. Targeted therapy for gastric cancer: Molecular pathways and ongoing investigations. *Biochimica et biophysica acta.—Reviews on Cancer* 1846, 232-237 (2014).
20. Shen, M. et al. Multifunctional drug delivery system for targeting tumor and its acidic microenvironment. *Journal of controlled release: official journal of the Controlled Release Society.* 161, 884-892 (2012).
21. Pan, B. F. et al. Synthesis and characterization of polyamidoamine dendrimer-coated multi-walled carbon nanotubes and their application in gene delivery systems. *Nanotechnology.* 20, 125101 (2009).
22. Qi, L. et al. Cell-Penetrating Magnetic Nanoparticles for Highly Efficient Delivery and Intracellular Imaging of siRNA. *Biomacromolecules* 13, 2723-2730 (2012).
23. Murphy, E. A. et al. Targeted nanogels: a versatile platform for drug delivery to tumors. *Molecular cancer therapeutics.* 10, 972-982 (2011).
24. Yu, X. & Pishko, M. V. Nanoparticle-based biocompatible and targeted drug delivery: characterization and in vitro studies. *Biomacromolecules.* 12, 3205-3212 (2011).
25. Zhou, J., Shum, K. T., Burnett, J. C. & Rossi, J. J. Nanoparticle-Based Delivery of RNAi Therapeutics: Progress and Challenges. *Pharmaceuticals* (Basel, Switzerland). 6, 85-107 (2013).
26. Guo, P. The emerging field of RNA nanotechnology. *Nature nanotechnology.* 5, 833-842 (2010).
27. Guo, P., Haque, F., Hallahan, B., Reif, R. & Li, H. Uniqueness, advantages, challenges, solutions, and perspectives in therapeutics applying RNA nanotechnology. *Nucleic acid therapeutics.* 22, 226-245 (2012).
28. Guo, P., Zhang, C., Chen, C., Garver, K. & Trottier, M. Inter-RNA interaction of phage phi29 pRNA to form a hexameric complex for viral DNA transportation. *Molecular cell.* 2, 149-155 (1998).
29. Shu, D., Moll, W. D., Deng, Z., Mao, C. & Guo, P. Bottom-up Assembly of RNA Arrays and Superstructures as Potential Parts in Nanotechnology. *Nano letters.* 4, 1717-1723 (2004).
30. Shu, Y. et al. Fabrication of 14 different RNA nanoparticles for specific tumor targeting without accumulation in normal organs. *RNA* (New York, N.Y.). 19, 767-777 (2013).
31. Shu, D., Shu, Y., Haque, F., Abdelmawla, S. & Guo, P. Thermodynamically stable RNA three-way junction for constructing multifunctional nanoparticles for delivery of therapeutics. *Nature nanotechnology.* 6, 658-667 (2011).
32. Abdelmawla, S. et al. Pharmacological characterization of chemically synthesized monomeric phi29 pRNA nanoparticles for systemic delivery. *Molecular therapy: the journal of the American Society of Gene Therapy.* 19, 1312-1322 (2011).
33. Zhang, H. et al. Crystal structure of 3WJ core revealing divalent ion-promoted thermostability and assembly of the Phi29 hexameric motor pRNA. *RNA* (New York, N.Y). 19, 1226-1237 (2013).
34. Shu, Y., Shu, D., Haque, F. & Guo, P. Fabrication of pRNA nanoparticles to deliver therapeutic RNAs and bioactive compounds into tumor cells. *Nature protocols.* 8, 1635-1659 (2013).
35. Haque, F. et al. Ultrastable synergistic tetravalent RNA nanoparticles for targeting to cancers. *Nano today.* 7, 245-257 (2012).
36. Khisamutdinov, E. F., Jasinski, D. L. & Guo, P. RNA as a boiling-resistant anionic polymer material to build robust structures with defined shape and stoichiometry. *ACS nano.* 8, 4771-4781 (2014).
37. Kalli, K. R. et al. Folate receptor alpha as a tumor target in epithelial ovarian cancer. *Gynecologic oncology.* 108, 619-626 (2008).
38. Teng, L., Xie, J., Teng, L. & Lee, R. J. Clinical translation of folate receptor-targeted therapeutics. *Expert opinion on drug delivery.* 9, 901-908 (2012).
39. Ly, A., Hoyt, L., Crowell, J. & Kim, Y. I. Folate and DNA methylation. *Antioxidants & redox signaling.* 17, 302-326 (2012).
40. Gao, W., Xiang, B., Meng, T. T., Liu, F. & Qi, X. R. Chemotherapeutic drug delivery to cancer cells using a combination of folate targeting and tumor microenvironment-sensitive polypeptides. *Biomaterials.* 34, 4137-4149 (2013).
41. Shi, J. et al. PEI-derivatized fullerene drug delivery using folate as a homing device targeting to tumor. *Biomaterials.* 34, 251-261 (2013).
42. Huang, P. et al. Folic acid-conjugated Silica-modified gold nanorods for X-ray/CT imaging-guided dual-mode radiation and photo-thermal therapy. *Biomaterials.* 32, 9796-9809 (2011).
43. Li, Z. M. et al. Aptamer-conjugated dendrimer-modified quantum dots for cancer cell targeting and imaging. *Materials Letter.* 64, 375-378 (2010).
44. Wang, Z., Ruan, J., Cui, D. X. Advances and Prospect of Nanotechnology in Stem Cells. *Nanoscale Resarch Letters.* 4, 593-605 (2009).
45. Song, H. et al. Anti-HIF-1 alpha antibody-conjugated pluronic triblock copolymers encapsulated with Paclitaxel for tumor targeting therapy. *Biomaterials.* 31, 2302-2312 (2010).

46. Huang, P. et al. Folic Acid-conjugated Graphene Oxide loaded with Photosensitizers for Targeting Photodynamic Therapy. *Theranostics*. 1, 240-250 (2011).
47. Chen, F. et al. The photoluminescence, drug delivery and imaging properties of multifunctional Eu3t/Gd3t dual-doped hydroxyapatite nanorods. *Biomaterials*. 32, 9031-9039 (2011).
48. Ma, J. B., et al. Folic Acid-Conjugated LaF3:Yb, Tm@SiO2 Nanoprobes for Targeting Dual-Modality Imaging of Upconversion Luminescence and X-ray Computed Tomography. *Journal Physical Chemistry C*. 116, 14062-14070 (2012).
49. Cui, D. et al. Characterization of BRCAA1 and its novel antigen epitope identification. *Cancer epidemiology, biomarkers & prevention: a publication of the American Association for Cancer Research, cosponsored by the American Society of Preventive Oncology*. 13, 1136-1145 (2004).
50. Yang, H. et al. Effect of blocking BRCAA1 gene with siRNA on proliferation of MCF-7 cells and expression of Rb gene. *Ch in J Cancer Biother*. 13, 181-184 (2006).
51. Li, C. et al. BRCAA1 antibody- and Her2 antibody-conjugated amphiphilic polymerengineered CdSe/ZnS quantum dots for targeted imaging of gastric cancer. *Nanoscale Res. Lett.* 9, 244 (2014).
52. Chen, L. et al. Tumor-specific Expression of MicroRNA-26a Suppresses Human Hepatocellular Carcinoma Growth via Cyclin-dependent and -independent Pathways. *Molecular Therapy*. 19, 1521-1528 (2011).
53. Fu, H. L. et al. TET1 Exerts Its Tumor Suppressor Function by Interacting with p53-EZH2 Pathway in Gastric Cancer. *J. Biomed. Nanotechnol*. 10, 1217-1230 (2014).
54. Chen, J. et al. Differential Expression of Phospholipase C Epsilon 1 Is Associated with Chronic Atrophic Gastritis and Gastric Cancer. *PLoS One*. 7, 10 (2012).
55. Jasinski, D. L., Khisamutdinov, E. F., Lyubchenko, Y. L., Guo, P. Physicochemically Tunable Polyfunctionalized RNA Square Architecture with Fluorogenic and Ribozymatic Properties. *ACS Nano*. 26, 7620-7629 (2014).
56. Khisamutdinov, E. F., et al. Enhancing immunomodulation on innate immunity by shape transition among RNA triangle, square and pentagon nanovehicles. *Nucleic Acids Res*. 42, 9996-10004 (2014).
57. Huang P, Bao L, Zhang C L, Lin J, Luo T, Yang D P, He M, Li Z M, Gao G, Fu S, Cui D. Folic acid-conjugated silica-modified gold nanorods for X-ray/CT imaging-guided dual-mode radiation and photo-thermal therapy. Biomaterials 2011; 32:9796-9809.
58. Ruan J, Wang K, Song H, Xu X, Ji J J, Cui D. Biocompatibility of hydrophilic silica-coated CdTe quantum dots and magnetic nanoparticles. Nanoscale Research Letters 2011; 6:299

What is claimed is:

1. An artificial RNA nanostructure molecule, comprising: a multiple branched RNA junction motif comprising at least one RNA oligonucleotide, and a gastric cancer targeting module coupled to the RNA junction motif, wherein the multiple branched RNA comprises sequence 5' UAGUGGGCCCUUUAUGUGG 3' (SEQ ID NO: 5).

2. The molecule of claim 1, further comprising at least one bioactive agent coupled to the RNA junction motif.

3. The molecule of claim 2, wherein the bioactive agent comprises a an siRNA, an miRNA, an anti-mRNA, a ribozyme RNAs, an antisense RNA, or a combination thereof.

4. The molecule of claim 3, wherein the siRNA is directed to Survivin, Bcl-2, XIAP, BCL-XL, or BRCAA1.

5. The molecule of claim 3, wherein the bioactive agent comprises siRNA sequence 5' GGACCACCGCAUCUC-UACAdTdT 3' (SEQ ID NO: 7), 5' dTdTCCUGGUG-GCGUAGAGAUGU 3' (SEQ ID NO: 8), 5'-AAGCUGu-CACAGAGGGGCUAC-3' (SEQ ID NO: 9), 5'GUAGCCCCUCUGUGACAGCUU-3 (SEQ ID NO: 10), 5'-CCAUGUGCUAUACAGUCAUUACUUU-3' (SEQ ID NO: 11), 5'-AAAGUAAUGACUGUAUAGCACAUGG-3' (SEQ ID NO: 12), 5'-UUGGACAAUGGACUGGUUGA-3' (SEQ ID NO: 13), 5'-UCAACCAGUCCAUUGUCCAA-3 (SEQ ID NO: 14), 5'-CCACAUAAAGGGCCCACUA-3' (SEQ ID NO: 15), 5'-UAGUGGGCCCUUUAUGUGG-3' (SEQ ID NO: 5).

6. The molecule of claim 3, wherein the bioactive agent is an anti-miRNA molecule for a miRNA comprising miR-9, miR-10b, miR-21, or miR-26.

7. The molecule of claim 3, wherein the bioactive agent is a miRNA molecule for a miRNA comprising let-7a, miR-10b, miR-25, miR-34a, miR-124, miR-145, or miR-181b.

8. The molecule of claim 2, wherein the bioactive agent comprises a drug, a fluorescent dye, a chemical, or a combination thereof.

9. The molecule of claim 2, wherein the bioactive agent is directed a gastric cancer marker.

10. The molecule of claim 1, wherein the nanostructure comprises at least one chemical modification at 2' position, wherein the chemical modification comprises 2' Fluoro, 2' Amine, and 2' 0-Methyl.

11. The molecule of claim 1, wherein the multiple branched RNA further comprises sequence 5' CCA-CAUAAAGGGCCCACUAuuCCCACAUACUUU-GUUGAUCC 3' (SEQ ID NO: 4).

12. The molecule of claim 1, wherein the multiple branched RNA junction motif is a three-branched RNA junction motif.

13. The molecule of claim 12, wherein the three-branched RNA junction motif comprises an a3WJ RNA module (SEQ ID NO: 1); a b3WJ RNA module (SEQ ID NO: 2); a c3WJ RNA module (SEQ ID NO: 3), or any combination thereof.

14. The molecule of claim 1, wherein the diameter of the molecule is at least about 40 nm or less.

15. The molecule of claim 1, wherein the molecule has zeta potential ranging from about −150 mV to about 150 mV.

16. The molecule of claim 1, wherein the molecule is substantially stable in a pH value ranges from about 2 to about 13.

17. The molecule of claim 1, wherein the gastric cancer targeting module comprises a ligand that binds to at least one gastric cancer cell surface marker.

18. The molecule of claim 17, wherein the ligand binds to a folate receptor, an epidermal growth factor receptor 2 (ErbB-2/HER2), an epidermal growth factor receptor (EGFR), a HER2 or a combination thereof.

19. The molecule of claim 18, wherein the targeting module is a folate.

20. The molecule of claim 17, wherein the ligand is an aptamer.

21. The molecule of claim 20, wherein the aptamer binds to EGFR, PDGFR, folate receptor, or a combination thereof.

22. The molecule of claim 21, wherein the ligand has sequence 5'-G CCU UAG UAA CGU GCU UUG AUG UCG AUU CGA CAG GAG GC-3' (SEQ ID NO: 6).

23. A composition comprising the artificial RNA nanostructure molecule of claim 1 and a pharmaceutically acceptable carrier.

24. A nanoparticle delivery system, comprising the artificial RNA nanostructure of claim 1 and a pharmaceutically acceptable carrier.

25. A method of treating gastric cancer in a subject having gastric cancer, comprising administering to the subject a therapeutically effective amount of a composition comprising the artificial RNA nanostructure of claim 1 and a pharmaceutically acceptable carrier.

26. An artificial RNA nanostructure molecule, comprising: a multiple branched RNA junction motif comprising at least one RNA oligonucleotide, and a gastric cancer targeting module coupled to the RNA junction motif, further comprising at least one bioactive agent coupled to the RNA junction motif, wherein the bioactive agent comprises siRNA sequence 5'-UAGUGGGCCCUUUAUGUGG-3' (SEQ ID NO: 5).

* * * * *

SEQUENCE LISTING

```
<160> NUMBER OF SEQ ID NOS: 20

<210> SEQ ID NO 1
<211> LENGTH: 18
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
uugccaugug uauguggg                                                         18

<210> SEQ ID NO 2
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
cccacauacu uuguugaucc                                                       20

<210> SEQ ID NO 3
<211> LENGTH: 16
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
ggaucaauca uggcaa                                                           16

<210> SEQ ID NO 4
<211> LENGTH: 41
<212> TYPE: RNA
```

```
<213> ORGANISM: Artificial Sequence
<220> FEATURE:
<223> OTHER INFORMATION: Description of Artificial Sequence: Synthetic
      oligonucleotide

<400> SEQUENCE: 4
ccacauaaag ggcccacuau ucccacauac uuuguugauc c                    41

<210> SEQ ID NO 5
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
uagugggccc uuuaugugg                                             19

<210> SEQ ID NO 6
<211> LENGTH: 39
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
gccuuaguaa cgugcuuuga ugucgauucg acaggaggc                       39

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 7
ggaccaccgc aucucuacat t                                          21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 8
ttccuggugg cguagagaug u                                          21

<210> SEQ ID NO 9
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
aagcugucac agaggggcua c                                          21
```

<210> SEQ ID NO 10
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10 guagcccuc ugugacagcu u                                              21

<210> SEQ ID NO 11
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11
ccaugugcua uacagucauu acuuu                                         25

<210> SEQ ID NO 12
<211> LENGTH: 25
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
aaaguaauga cuguauagca caugg                                         25

<210> SEQ ID NO 13
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
uuggacaaug gacugguuga                                               20

<210> SEQ ID NO 14
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
ucaaccaguc cauugccaa                                                20

<210> SEQ ID NO 15
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
ccacauaaag ggcccacua                                                19

<210> SEQ ID NO 16
<211> LENGTH: 21
<212> TYPE: RNA
<213> ORGANISM: Artificial Sequence
<220> FEATURE:
<223> OTHER INFORMATION: Description of Artificial Sequence: Synthetic
    oligonucleotide

<400> SEQUENCE: 16
uagugggccc uuuauguggu u        21

<210> SEQ ID NO 17
<211> LENGTH: 18
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 17
accaaatctc ccgcaagg        18

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 18
catattttcc aggtccgaca        20

<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 19
gaaggtgaag gtcggagtc        19

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 20
gaagatggtg atgggatttc        20